(12) United States Patent
Stark et al.

(10) Patent No.: US 7,318,907 B2
(45) Date of Patent: Jan. 15, 2008

(54) SURFACE PLASMON ENHANCED ILLUMINATION SYSTEM

(75) Inventors: Peter Randolph Hazard Stark, Andover, MA (US); Dale N. Larson, Waban, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 946 days.

(21) Appl. No.: 10/218,928

(22) Filed: Aug. 14, 2002

(65) Prior Publication Data

US 2003/0036204 A1 Feb. 20, 2003

Related U.S. Application Data

(60) Provisional application No. 60/312,214, filed on Aug. 14, 2001.

(51) Int. Cl.
*C12Q 1/68* (2006.01)
*G01N 15/06* (2006.01)
*G01N 33/00* (2006.01)
*G01N 33/48* (2006.01)
*G01N 35/00* (2006.01)

(52) U.S. Cl. .............. 422/50; 422/55; 422/58; 422/68.1; 422/82.05; 422/82.08; 422/82.07; 422/82.09; 436/43; 436/63; 436/164; 436/172; 73/1.01; 73/1.02; 29/592; 29/592.1; 250/491.1; 250/492.1; 250/493.1

(58) Field of Classification Search ............ 250/491.1, 250/492.1, 493.1; 422/50, 55, 58, 68.1, 82.05, 422/82.08, 82.07, 82.09; 436/43, 63, 164, 436/172; 29/592, 592.1; 73/1.01, 1.02
See application file for complete search history.

(56) References Cited

U.S. PATENT DOCUMENTS

| 5,973,316 | A  | 10/1999 | Ebbesen et al. |
| 6,052,238 | A  | 4/2000  | Ebbesen et al. |
| 6,236,033 | B1 | 5/2001  | Ebbesen et al. |
| 6,285,020 | B1 | 9/2001  | Kim et al.     |

OTHER PUBLICATIONS

Ebbesen, T. W., Lezec, H. J., Ghaemi, H. F., Thio, T. & Wolff, P. A. Extraordinary optical transmission through sub-wavelength hole arrays. Nature 391, 667-669 (1998).

(Continued)

*Primary Examiner*—Brian Sines
(74) *Attorney, Agent, or Firm*—Wolf, Greenfield & Sacks, P.C.

(57) ABSTRACT

Methods and apparatus for producing small, bright nanometric light sources from apertures that are smaller than the wavelength of the emitted light. Light is directed at a surface layer of metal onto a light barrier structure that includes one or more apertures each of which directs a small spot of light onto a target. The incident light excites surface plasmons (electron density fluctuations) in the top metal surface layer and this energy couples through the apertures to the opposing surface where it is emitted as light from the apertures or from the rims of the apertures. Means are employed to prevent or severely limit the extent to which surface plasmons are induced on the surface at the aperture exit, thereby constraining the resulting emissions to small target areas. The resulting small spot illumination may be used to increase the resolution of microscopes and photolithographic processes, increase the storage capacity and performance of optical data storage systems, and analyze the properties of small objects such as protein and nucleic acid molecules and single cells.

86 Claims, 9 Drawing Sheets

OTHER PUBLICATIONS

Ghaemi, H. F., Thio, T., Grupp, D. E., Ebbessen, T. W. & Lezec, H. J. Surface plasmons enhance optical transmission through subwavelength holes. Phys. Rev. B 58, 6779-6782 (1998).

Kim, T. J., Thio, T., Ebbessen, T. W., Grupp, D. E. & Lezec, H. J. Control of optical transmission through metals perforated with subwavelength hole arrays. Opt. Lett. 24, 256-258 (1999).

Grupp, D. E., Lezec, H. J., Ebbessen, T. W., Pellerin, K. M. & Thio, T. Crucial role of metal surface in enhance transmission through subwavelength apertures. App. Phys. Lett. 77, 1569-1571 (2000).

Sönnichsen, C., Duch, A. C., Steininger, G., Koch, M. & Plessen, G. V. Launching surface plasmons into nanoholes in metal films. App. Phys. Lett. 76, 140-142 (2000).

Sandoz, P., Giust, R. & Tribillon, G. Multi-aperture optical head for parallel scanning near field optical microscopy. Opt. Commun. 161, 197-202 (1999).

Grupp, D. E., Lezec, H. J., Thio, T. & Ebbessen, T. W. Beyond the Behta Limit: Tunable Enhanced Light Tranmsission Through a Single Sub-Wavelength Aperture. Adv. Mater. 11, 860-862 (1999).

Strelniker, Y. M. & Bergman, D. Optical transmission through metal films with a subwavelength hole array in the presence of a magnetic field. Phys. Rev. B 59, 12763-12766 (1999).

Raether, H. Surface Plasmons on Smooth and Rough Surfaces and on Gratings (Springer-Verlag. 1988).

Lezec, H. J. et al. Beaming light from a subwavelength aperture. Science 297, 820-822 (2002).

Jung, L.S., Campbell, C.T., Chinowsky, TM, Mar, M.N. & Yee, S.S. Quantitative Interpretation of the Response of Surface Plasmon Resonance Sensors to Adsorbed Films. Langmuir, vol. 14, No. 19, 5636-5648 (1998).

Thio, T., Pellerin, K.M. & Linke, R.A. Enhanced light transmission through a single subwavelength aperture. Optics Letters, vol. 26, No. 24, 1972-1974(2001).

SURFACE PLASMON ENHANCED ILLUMINATION SYSTEM

CROSS REFERENCE TO RELATED APPLICATIONS

This application claims the benefit, under 35 U.S.C. §119(e), of the filing date of U.S. Provisional Application Ser. No. 60/312,214 filed on Aug. 14, 2001.

FIELD OF THE INVENTION

This invention relates to methods and apparatus in which target areas are illuminated with one or more spots or lines of light having very small dimensions and the use of these spots or lines of light and changes to them as a sensing technique.

BACKGROUND OF THE INVENTION

Typical optical microscopy, far-field light microscopy, cannot resolve distances less than the Rayleigh limit. The Rayleigh criterion states that two images are regarded as just resolved when the principal maximum (of the Fraunhofer diffraction pattern) of one coincides with the first minimum of the other [see Born, M. and Wolf, E. *Principles of Optics*. Cambridge University Press $6^{th}$ ed. p.415 (1980)]. For a circular aperture, this occurs at $$w = 0.61 \frac{\lambda}{NA}$$

For example, the wavelength ($\lambda$) at the peak emission of a green fluorescent protein (EGFP) is 508 nm. Hence, for a very high numerical aperture (NA) of the objective, NA of 1.4, the minimum separation (w) that can be resolved in a GFP labeled sample is 221 nm. Currently, there are several possible methods for achieving resolution of spatial locations of proteins below the Rayleigh limit. They include: Confocal Microscopy, Fluorescence Resonance Energy Transfer (FRET), Atomic Force Microscopy (AFM), Near-Field Scanning Optical Microscopy (NSOM), Harmonic Excitation Light-Microscopy (HELM), Stimulated Emission Depletion Microscopy (STED-Microscopy) and Electron Microscope Immunocytochemistry.

Confocal Microscopy is a technique in which a very small aperture(s) is/are placed in the optical path to eliminate any unfocused light. This allows for a substantial increase in signal to noise ratio over conventional light microscopy. Also, it is possible to reduce the width of the central maximum of the Fraunhoffer pattern using a small slit or aperture. This, in turn allows a substantially enhanced resolution of 1.4 times better than the Rayleigh limit. Therefore, with this method, using the above protein as an example, a spatial resolution of 156 nm is achieved.

Typical confocal microscopy is not without disadvantages. By increasing the signal to noise ratio by decreasing the aperture size, the total signal level decreases concurrently. To bring the signal back to a useful level, the input power level must be increased. This, in turn, not only can cause photo-bleaching in the fluorophores at which one intends to look but also the surrounding area where the light is incident, just not collected. A method around this is to use two-photon excitation. Fluorescence from the two-photon effect depends on the square of the incident light intensity, which in turn, decreases approximately as the square of the distance from the focus. Because of this highly nonlinear (~fourth power) behavior, only those dye molecules very near the focus of the beam are excited, while the surrounding material is bombarded only by comparatively much fewer of the low energy photons, which are not of enough energy to cause photo bleaching. Multi-photon excitation requires highly skilled technicians and is somewhat expensive for clinical use. Because it acquires only a small area at once, the surface must be scanned in three dimensions for mapping.

Fluorescence Resonance Energy Transfer (FRET) can provide exquisite resolution of single chromophores. The resonance occurs when one fluorophore in an excited state transfers a portion of its energy to a neighboring chromophore. For this to take place, there must exist some overlap between the emission spectrum of the fluorophore to absorption spectrum of the chromophore (the frequency of the emission spectrum should be somewhat higher than the absorption spectrum of the chromophore). The process does not occur through photonic emission and absorption but through a dipole-dipole interaction. The strength of the interaction varies as $r^{-6}$. The Forster distance [see Forster, T Discuss. *Faraday Soc.* 27 7-29 (1959)] is the distance at which the efficiency of the transfer is such that there exists equal probability that the fluorophore loses energy to radiative decay or dipole-dipole interaction. The Forster distance, essentially, is the threshold at which FRET will no longer exist for a given pair. Typically the Forster distance is between 3 and 6 nm [see Pollok & Heim "Using GFP in FRET-based Applications" *Trends in Cell Biology* 9 pp57-60 (1999)].

By placing either of the complementary pair near the other, resolutions of less than the Forster distance can be attained. The problem with this technique in determining relative locations is that one of the pair needs to be located within the resolution tolerances desired for spatial mapping. This can be achieved by placing one of the pair on a probe used in either atomic force microscopy (AFM) or near-field scanning optical microscopy (NSOM). Another problem is that dipole-dipole interactions are dependent on the relative orientation of the two. To maximize signal from the interaction would require a 3D scan around one of the pair.

Atomic Force Microscopy (AFM) can be envisioned as a very small (usually metal) stylus dragged across a surface giving feedback as to the height, Z, of the stylus relative to the surface. Resolution can be as fine as the scanning step size (typically 5 nm). By scanning across the surface, X and Y coordinates are obtained provided that the origin remains fixed (i.e., that there is no drift in the translation stage due to thermal or other effects). There are many methods for ensuring that the stylus does not actually contact the sample but maintains very accurate resolution of the Z coordinate. Because only surface morphology is measured, differentiating several molecules can be extremely difficult unless the dimensions and orientations of those molecules are well known. A solution to this might be to add tags of discrete lengths or shapes, which could be bound indirectly to the molecules of interest. This method, however, would require that the tissue sample to be planar before the tags were bound to the surface.

To increase the information of AFM, one could use Near-Field Scanning Optical Microscopy (NSOM or SNOM). NSOM uses a principle similar to AFM in which a stylus is scanned over a surface providing topographical information. However, the stylus is a conductor of photons. By emitting light from the tip of the stylus, optical measurements such as fluorescence can be obtained. Most often, these styli are fiber probes that have tapered tips and then are plated with a conductive material (aluminum is most often chosen as its skin depth for optical radiation is quite low, ~13 nm at 500 nm) with a small aperture where the coating is broken. [See Betzig & Trautman "Near-Field Optics: Microscopy, Spectroscopy, and Surface Modification beyond the Diffraction Limit" *Science* 257 pp189-195 (1992)]. Another approach is to use what are called "apertureless probes" [see Sanchez, Novotny and Xie "Near-Field Fluorescence Microscopy Based on Two-Photon Excitation with Metal Tips" *Physical Review Letters* Vol 82 20 pp 4014-4017 (1999)] where an evanescent wave is excited by bombardment with photons at the tip of a sharpened metal probe. Because the tip can be made very sharp (radii of 5 nm are achievable), resolutions can be correspondingly smaller. An associated problem with the "apertureless probes" is that the probe generates a white light continuum, which significantly decreases the signal to noise ratio.

By making the diameter (assuming a circular geometry) of the emission portion of the tip of the stylus very small (smaller than resolution desired) and keeping the tip to sample distance less than that distance, so that the diffraction is small, a nanometric light source is available. This light source can be used to excite fluorescence in the sample. Because the size of the source is very small and the scanning increments are also very small, highly resolved information on spatial locations of the fluorophores can be gleaned by inspection in the far field. Alternatively, the probe can be used for collection, measuring fluorescence or reflection or even transmission from illumination from the other side of the sample.

Because the aperture size in a conventional probe is so much smaller than the wavelength of the excitation light and only an evanescent mode is supported, very little light is transmitted through the aperture. Diffraction effects limit the effective collimated length from the aperture to less than diameter of the aperture. This, then, requires that the aperture be held below a maximum height above the surface of the sample. Ideally, a fixed height above the surface (usually less than 10 nm) is used for relative contrast measurements. The height of the aperture relative to the surface is kept constant by measuring the shear force on the tip of the probe or by optical methods and is modulated to maintain that height. For this reason, NSOM is particularly susceptible to vibrations and experimental work requires isolation platforms.

Scanning the surface takes a fair amount of time. Thermal drift in commercially available open and closed loop nanometric scanning stages is about 20-30 nm/min. [see Frohn, Knapp and Stemmer "True optical resolution beyond the Rayleigh limit achieved by standing wave illumination" *Proceedings of the National Academies of Science* Vol. 97, 13 pp 7232-7236 (2000)]. This can be severely limiting if scanning time is more than a few tens of seconds and resolution less than 50 nm is desired. If the surface is scanned for several different types of molecules, the required time to investigate a single cell becomes far too large for use in a clinical setting and would require multiple homings of the scanning stage. An approach to diminishing the scanning time may be to scan with multiple probes concurrently. This approach would be limited to just a few probes as on a small ($20^2$ μm$^2$) surface, the relatively large size of the probes' bodies would interfere mechanically with each other.

U.S. Pat. Nos. 5,973,316 and 6,052,238 issued to Ebbesen et al. of the NEC Research Institute, Inc. describe a NSOM device which employs an array of subwavelength apertures in a metallic film or thin metallic plate. Enhanced transmission through the apertures of the array is greater than the unit transmission of a single aperture and is believed to be due to the active participation of the metal film in which the aperture array is formed. In addition to enhancing transmission, the array of apertures reduces scanning time by increasing the number of nanometric light sources.

A second method for increasing the number of light sources illuminates the sample with a mesh-like interference pattern and by post processing of the images. In Harmonic Excitation Light Microscopy (HELM), a laser is split into four beams and two of those beams modulated to produce an extended two-dimensional interference field with closely spaced antinodes. By introducing the beams at an angle to the surface to be imaged, an effective offset in reciprocal space is produced around an origin. If four images are taken around this origin and one at the origin, it is possible to construct, with post processing, a smaller single antinode which acts as a nanometric light source. This process can result in a lateral resolving power of close to 100 nm or half of the Rayleigh distance for green light. Because only a few images are required to map an entire surface, the acquisition time is extremely short (around 1.6 s for a 25 μm×25 μm area with 100 nm resolution.) Due to the required precision in the location of the four images around the origin and the drift associated with the scanning stage, it is unlikely that the resolution will be dramatically increased.

Another new form of microscopy is that introduced by Klar et al. [see Klar, Jakobs, Dyba, Egner and Hell "Fluorescence microscopy with diffraction resolution barrier" *Proceedings of the National Academies of Science* Vol 97 15 pp 8206-8210 (2000)] called Stimulated Emission Depletion (STED) Microscopy. STED microscopy is based on a method of quenching fluorescence by stimulated emission depletion reducing the fluorescing spot size. [See Hell & Wichmann "Breaking the Diffraction Resolution Limit by Stimulated-Emission-Depletion Fluorescence Microscopy" *Opt. Lett* 19 11 780-782 (1994); Lakowicz, Gryczynski, Bogdanov and Kusba. "Light Quenching and Fluorescence Depolarization of Rhodamine-B and Applications of this Phenomenon to Biophysics" *J. Phys. Chem.* 98 1 334-342 (1994); Hell, S. W. *Topics in Fluorescence Spectroscopy*, ed. Lakowicz (Plenum Press, NY), Vol. 5, pp. 361-422; and Klar & Hell "Subdiffraction resolution in far-field fluorescence microscopy" *Opt. Lett* 24 14, 954-956 (1999)]. Fluorescence can be quenched by subjecting a fluorophore to light at the lower energy edge (red side) of its emission spectrum. This forces the fluorophore to a higher vibrational level of the ground state, which, by decay of that state prevents re-excitation. Fluorescence can be turned on, with an ordinary excitation source, and turned off, with the STED beam, at will. By introducing an interference pattern in the STED beam, a local set of maxima and minima can be created. If the maxima of the STED beam are overlaid onto the fluorescence induced by the excitation beam, the fluorescence is quenched. However, where the minima occur, fluorescence continues. The fluorescing spot size is controlled by the union of the minimum or minima of the STED beam and the maximum of the excitation beam. Because STED is nonlinear with intensity, the sharpness of the minimum, maximum transition can be effectively increased allowing a narrow, almost delta behavior to be displayed. This, however, can result in severe photo stress to the sample and, possibly, dual photon effects, causing competing modes in the area where quenching is desired. So far, resolution in the radial (X,Y) direction is around 100 nm, but there is no reason to expect that the resolution can't be substantially improved. Once again, though, STED microscopy is a scanning type and will suffer from the same drawbacks all scanning instruments do, (e.g., thermal drift, vibration problems, registration of near field excitement with far field collection and scan time.)

SUMMARY OF THE INVENTION

The present invention contemplates a different technique to achieve sub-Rayleigh criterion resolution, which is here called "Surface Plasmon Enhanced Illumination" (SPEI). SPEI is related to NSOM in that nanometric light sources are created by subwavelength apertures. By applying the principles of the present invention, a significant reduction in the size of the area illuminated by each aperture is achieved, resulting in significantly improved resolution.

The present invention takes the form of methods and apparatus that employ novel physical structures to provide nanometric spot or line illumination. In accordance with the invention, one or more apertures are formed through a first planar conductive material. Each aperture (which may be either a hole or a slit) has at least one cross-sectional dimension which is less than the wavelength of light which is incident to the planar material. In accordance with a feature of the invention, the structure includes means for confining the electronic excitation induced in that portion of the planar surface near the end of the aperture from which the light exits.

The conductive plane that receives the incident light may be placed on one outer surface of a dielectric material. The dielectric material's interface with the conductive plane that receives the incident light establishes a substantially different effective dielectric function in that interface than that of the conductive plane that receives the incident light. This difference in effective dielectric function prevents the excitation of large densities of surface plasmons in non-illuminated plane of the metal if monochromatic light is used at the resonant wavelength of the illuminated metallic plane. Therefore light should not be substantially emitted from the non-illuminated metallic plane.

Alternatively, the sidewalls of the aperture may be conductive to conduct excitation currents and act as a pseudo-waveguide for the light traveling through the aperture. At the exit end of the aperture, the amount of exposed conductive material is limited to an area immediately surrounding the hole exit by a dielectric material, or by a groove cut into the surface of the conductive material at the exit plane to a depth substantially deeper than the skin depth of the induced excitation and of such width and spacing to prevent an unwanted resonance of surface plasmons in that surface.

Alternatively, the conductive plane that receives the incident light may take the form of a "good metal" layer with a "bad metal" layer having significantly different dielectric properties being sandwiched between the good metal layer and a dielectric substrate. The bad metal layer is preferably opaque to the light to be emitted from the surface of the good metal and its resonance (as determined by its dielectric function, the surface roughness and the dielectric functions of the materials on either side of the bad metal layer) should be very different from the resonance of the "good" metal, such that at desired frequency, light transmitted is emitted only from the holes and not from the exit surface of the array. The insulating dielectric substrate ensures that there can be no surface plasmon excitation from the good metal layer through the light barrier. When a bad metal layer is used that is both opaque to light and has sufficiently different dielectric properties relative to the good metal to eliminate resonant coupling, the dielectric insulator may be eliminated.

The present invention substantially reduces, compared to an array of subwavelength apertures in a monometallic film such as those described by Ebbesen et al., the size of the area of illumination produced by each aperture using the combination of a metallic layer on which surface plasmons are induced by incident light and surface composed of a material of substantially different dielectric function, such as an insulator or a different metal, so that the excitation of the surface plasmons in the light emitting surface in the exit surface layer will be different than those excited in the metallic layer that is excited by the incident light, and only the light from the decaying resonant surface plasmons of the exit layer will emit from that surface. The photons associated with the resonance of the incident or upper surface will be constrained to exit from the hole itself or from the walls of the hole.

In accordance with the invention, the light barrier comprises an illuminated surface consisting of a continuous conductive metallic layer in combination with an exit layer having substantially different dielectric properties. One or more apertures through the barrier (one or more holes or slits) then form "photonic funnels" through the barrier. Note that confining or eliminating electronic surface excitation on the surface opposite to the illuminated surface works with a single aperture as well as an array of apertures.

The invention may advantageously take the form of an array of apertures (holes or slits) formed in structure consisting of a dielectric substrate coated with a conductive metal film on one or both surfaces, or by a thick metallic film, and which further incorporates means for confining the electronic surface excitation to an area immediately adjacent to the apertures where light exits the structure. The means for confining the electronic surface excitation preferably takes the form of a layer of material having dielectric properties that differ substantially from those of the illuminated metal layer, and may consist of a dielectric insulator, a "bad metal" having different dielectric properties, grooves or surface irregularities at the exit surface, or a combination of these. The structure which confines the electronic surface excitation restricts the size of the spot or line of illumination from each aperture, and the use of an array of apertures, or an array of surface irregularities on the metal film, increases the intensity of the illumination from each aperture The present invention may also be applied to advantage in an optical data storage device. Several arrangements may be devised for combining the hole array with some medium for data storage. A light source, such as a laser, may be directed onto the front surface of the hole array which collects and funnels the array of light onto an optical storage medium. The bit value stored at each position in the storage medium controls the propagation of light through the storage medium to an adjacent pixel position in a charge coupled device (CCD) or other area detectors. A translation mechanism effects movement of the storage medium relative to the hole array in incremental steps, with each step distance being equal to the aperture size. In an alternative arrangement, data may be represented by illumination levels, such as gray scale values or color levels, and optical means may be used in place of or to supplement the mechanical translation mechanism.

The well defined and highly concentrated areas of illumination created by using such a structure as a light source provide significant advantages in microscopy and in optical data storage devices. The confined illumination patterns produced in accordance with the invention may be used to construct a "Surface Plasmon Enhanced Microscope" (SPEM) exhibiting markedly improved resolution, to construct an optical data storage device capable of storing larger amounts of data in optical storage media with much higher data access rates than is achievable with current optical data storage devices, and to provide a high throughput photolithography technique that can be applied to advantage in semiconductor fabrication and patterning for self-assembly and biological applications.

A further embodiment of the invention provides an improved system for analyzing one or more small objects. A radiation barrier having one or more sub-wavelength apertures is positioned between a source of radiation and a radiation sensor. The object to be analyzed is positioned in the pathway of the radiation that flows through an aperture and the radiation level at the sensor is measured to evaluate one or more properties of the object. The barrier includes a conductive surface which is illuminated by incident radiation from the source to produce surface plasmons, and means are preferably employed to limit the extent to which surface plasmons are induced on the opposite surface adjacent the radiation detector, thereby focusing the light on the sensor. The presence of the object alters the radiation received at the sensor in way that may be measured to determine the property of the small object or objects. This technique may be employed to advantage to evaluate biological macromolecules, including protein molecules and nucleic acid molecules, as well as single cells or organisms and spores.

Means may be employed for moving macromolecules or other small object(s) to be analyzed toward and through the aperture as measurements are being taken. To this end, the small objects may be contained in a carrier fluid which flows through the aperture or apertures. The objects may be charged and an electrostatic field may be applied to the objects to cause them to move through the aperture, or a microfluidics system may be used to feed a solution containing the macromolecules toward and through the aperture or apertures as measurements are taken. The radiation sensor may detect changes in the intensity of the radiation caused by the presence of the small object(s), or changes in the spectral content of the radiation may be measured to detect fluorescence of the objects being measured, changes in the radiation pattern emitted from an aperture or apertures may be measured, or changes in resonance caused by the presence of the micromolecules near the conductive surface of the radiation barrier may be measured. The data thus collected may be processed to yield information about the size, shape, orientation, fluorescence, absorbance, and transmission characteristics of the objects being analyzed.

In a still further embodiment of the invention, a radiation barrier interposed between a light source and a detector may be used to analyze ligands that are immobilized on the surface barrier. The ligands' binding partners bind to the ligands immobilized on the illuminated surface and, as that occurs, or after it has occurred, a shift in resonance or other measurable change is measured. In addition the binding of small molecules to proteins, post translational modifications of proteins, protein-protein interactions, and the binding of nucleic acids can all be detected.

These and other objects, features and advantages of the present invention may be better understood by considering the following detailed description of specific embodiments of the invention. In the course of this description, reference will frequently be made to the attached drawings.

DETAILED DESCRIPTION

As described in U.S. Pat. Nos. 5,973,316 and 6,052,238 issued to Ebbesen et al., enhanced light transmission occurs through an array of apertures in a metal film due to the surface plasmons induced in the conductive film by the incident light.

Figure 1:
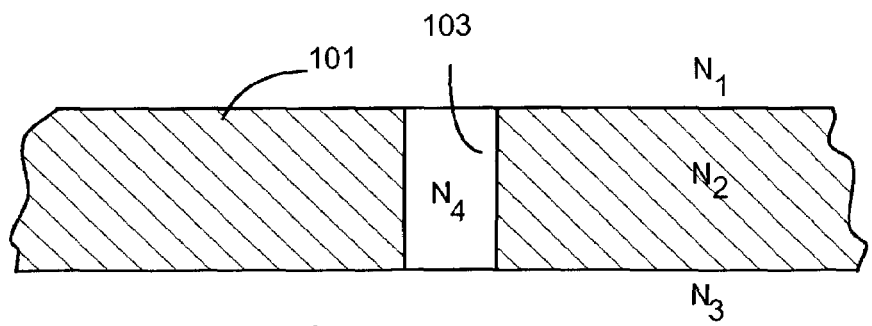
FIG. 1 is a cross-sectional view of an aperture through a metallic film, the film being substantially thicker than the skin depth within which an optically induced electronic excitation occurs, and the aperture having a diameter less than the wavelength of the incident light.

FIG. 1 shows a cross section of an optically thick metal film 101. The term "optically thick" means that the thickness of the film 101 is greater than two times the skin depth. For all essential purposes, this means that there is no direct coupling of the surface plasmons (coherent collective excitations of electrons) at the upper surface (the interface between media of index $N_1$ and $N_2$) and the lower surface (the interface between media of index $N_3$ and $N_2$). In a typical case, the indices $N_1$, $N_3$, and $N_4$ are equal while $N_2$, the index of the metal film 101, is substantially different and the metal film 101, unlike the surrounding material, is a conductor of electronic charges.

If the array spacing and the dielectric functions and thickness of the metals and substrates are tailored to attain a high transmission, a significantly higher power density than that transmitted through the single aperture probe used in NSOM (a ratio of about one million per aperture for a 50 nm holes) can be delivered through the apertures. This substantially increases the signal to noise ratio of surface plasmon enhanced microscopy (SPEM) over the NSOM at normal resolutions and is allows a smaller hole size to be used, providing better resolution and dramatically decreasing the dwell time required for an adequate signal to be received.

Unfortunately, the coupling (indirect or direct) between the surfaces of the film 101 seen in FIG. 1 have effects that adversely affect desired resolution. Sönnichsen et al., "Launching surface plasmons into nanoholes in metal films", *App. Phys. Lett.* 76, 140-142 (2000) show that, when gold, silver or aluminum films are struck with plane polarized light, surface plasmons are induced in the direction of the polarization. When the plasmons encounter a hole, the coupling to the other side results in light emitted in a prolate shape of a major dimension of about an order of magnitude larger than the hole size. The prolate shape is caused by the radiative decay of the surface plasmons and is a function of the dielectric function of the metal and the wavelength of the incident light and if significant surface roughness exists, the distance between the elements of roughness on that plane.

With a simple isotropic periodically perforated metal film, two potential problems are encountered. First, for use in a microscope and other applications (e.g. optical data storage and photolithography) where small sources of light (high resolution) are required, the existence of the associated prolate pattern diminishes resolution in one dimension severely. Second, the array spacing would have to be such that patterns did not interfere or overlap. Achieving the appropriate spacing would in turn cause the wavelengths at which the surface plasmons are resonant to be shifted, resulting in resonant wavelengths of lower energy. For the excitation of commonly available fluorophores, multi-photon (probably three or four) excitation would be required. Of course, the prolate pattern could simply be accepted and the resolution in the direction of the polarization (along the major axis of the pattern) would default to that dictated by the Rayleigh criterion for that wavelength and numerical aperture.

If a smaller spot illumination size (a nanometric light source) is required, the prolate shape generated from the geometry shown in FIG. 1 is undesirable. If the incident light is polarized, the long dimension of the pattern shape is probably only loosely dependent on the hole size and more dependent on the surface roughness, since rougher surfaces act as very small antennae, which cause SPs to decay, spatially, more rapidly than would be the case if the film surface were smooth. Moreover, the frequency of the light will also affect the pattern shape. Note also that the preferred shape of the intensity pattern for spot illumination should exhibit a step function rather than the extended somewhat gaussian pattern that is seen along the major axis of the prolate shape.

In accordance with the present invention, novel structures are used to minimize or eliminate the prolate pattern described above. If the emitting surface (bottom) is no longer continuous but is instead constructed to constrain the propagation of surface plasmons to the immediate vicinity of the aperture, the size of the resulting area of illumination is significantly reduced. If the illuminated surface (top) is left as a continuous conductor with an array of circular holes in it and the bottom is segmented as described above, a photonic funnel can be created. To minimize the effective broadening of the holes due to surface plasmons on the bottom plane, it may be desirable to create a very sharp edge at this point in either a conducting wall or in an insulator with less available charge to minimize any surface-plasmons/photon interaction. It is important to note that the insulator (in the case of a semiconductor) should have a band gap significantly larger than the frequency of the photons, which will be propagating through it.

Figure 4:
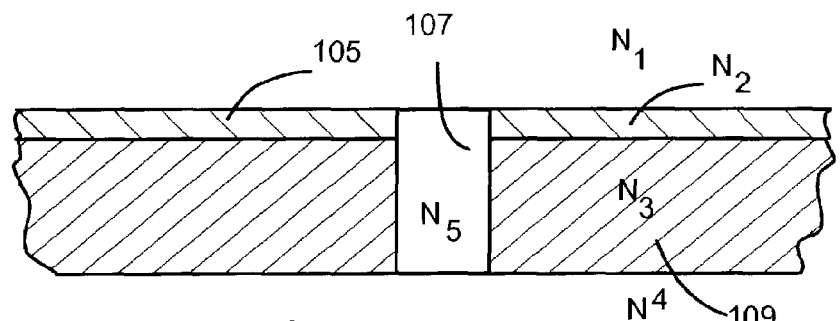
FIG. 4 is a cross-sectional view of a thin metallic film that covers a non-metallic substrate material with an aperture through both the metal film and substrate having a diameter less than the wavelength of the incident light.

A first improved geometry for the hole array that produces a smaller illumination pattern is shown in FIG. 4 of the drawings. A thin metal conductive film 106 exhibiting the index $N_2$ is affixed to a substrate 109 constructed of a dielectric material having the index $N_3$ and a bandgap that is larger than the frequency of the illumination of light. The dielectric substrate 109 can be constructed of a material that is transparent (but need not be) to light at the frequency employed, such as quartz or glass. Note that the aperture 107 need not go through the dielectric substrate if it is transparent, and such a structure may be easier to fabricate. The substrate should have a small index of refraction $N_3$ compared to the index of the metal $N_2$. Note also, as discussed later in connection with FIG. 20, that a "bad metal" having poor conductivity at these frequencies (such as tungsten) may be used in place of the dielectric 109 in combination with a "good metal" illuminated layer (such as aluminum). In fluorescence studies, if multi-photon excitement is employed, the bandgap should be larger than the sum of the photonic energies of the photons that would be simultaneously absorbed by the fluorophore. The thin layer of conducting material 105 should be thicker than the skin depth of the metal at the chosen wavelengths. The geometry and composition of the heterogeneous structure seen in FIG. 4 should be chosen so that a maximum of transmission of illumination occurs through the hole 107 at the chosen illumination wavelength. A tunable or broad band light source may also be used to tune the wavelength to predetermined hole dimensions.

Figure 5:
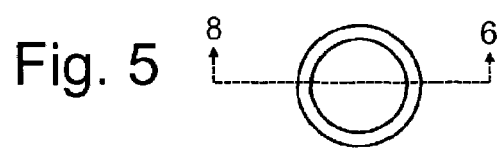
FIG. 5 is a view illustrating the approximate size of the circular area illuminated by the light transmitted through the aperture in structure shown in FIG. 4.
Figure 6:
FIG. 6 is a graph illustrating the illumination intensity in the illuminated area taken along the line 6-6 of FIG. 5.

The advantage of the geometry shown in FIG. 4 over that presented in FIG. 1 results from the fact that there is no coupling of plasmons from the upper surface of the film 105 to the lower surface of the dielectric material 109. This reduced coupling creates a smaller and more defined illumination pattern with steeper side slopes as illustrated in FIGS. 5 and 6. It is unclear, though, what happens to the energy at the corner interface of the hole 107, the metal film 105 and the dielectric substrate 109, that is, at the boundary of the materials having the indices N5, N2 and N3. If N1, N4 and N5 are not all substantially equal to one (1.0), combinations of differing indices could be used to tailor the transmission of the array apertures for a specific wavelength or method of illuminating the structure. For example, N, could be the index associated with an optical fiber, which would be coupled to a remote light source.

Figure 7:
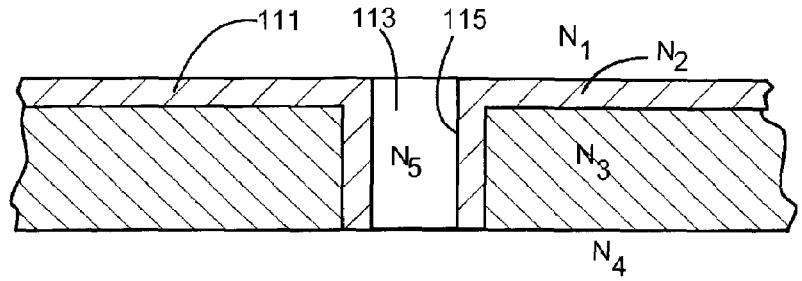
FIG. 7 is a cross-sectional view of a thin metallic film that covers the surface of a non-metallic substrate material as well as the sidewalls of an aperture through the substrate with the aperture having a diameter less than the wavelength of the incident light.
Figure 8:
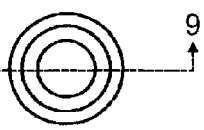
FIG. 8 is a view illustrating the approximate size of the circular area illuminated by the light transmitted through the aperture in the structure shown in FIG. 7.
Figure 9:
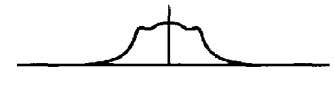
FIG. 9 is a graph illustrating the illumination intensity in the illuminated area taken along the line 9-9 of FIG. 8.

A second hole array structure for reducing the size and increasing the density of the spot illumination is shown in FIG. 7. As before, the structure of FIG. 7 presents at its upper surface a continuous conducting thin film metallic film 111 having the index $N_2$. The structure differs from that shown in FIG. 4 in that the metallic coating is continued into the interior of the hole 113 as seen at 115. If the thickness of metal layer 115 in the hole interior were greater than skin depth, the effects seen in optically thick metal films as shown in FIG. 1 would be duplicated from the standpoint of optical transmission through the holes. However, a smaller and more concentrated output light pattern is achieved by limiting the propagation length of SPs at the exit surface to the thickness of the film in the hole. Limiting the size of the excited surface area surrounding the hole exit produces a concentrated, circular light pattern as seen in FIG. 8 rather than prolate pattern seen in FIG. 3, thus limiting the size of the light source in only one of its two dimensions. As is the case with the structure shown in FIG. 4, the indices $N_1$, $N_4$ and $N_5$ may be equivalent to 1 in the simplest configuration but other combinations be used to tune the holes for a specific resonance. FIG. 9 graphs the steeply skirted intensity distribution expected across the circular light pattern along the line 9-9 of FIG. 8.

Figure 10:
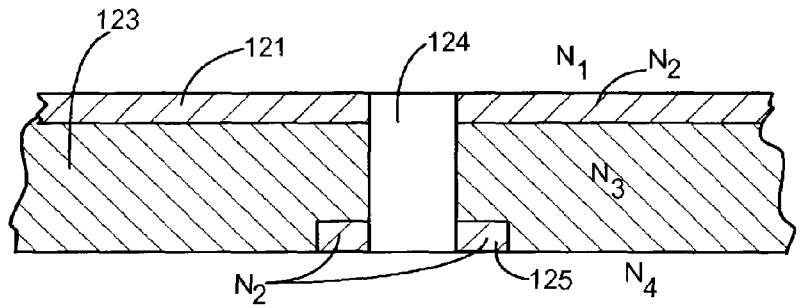
FIG. 10 is a cross-sectional view of a thin metallic film which covers a non-metallic substrate material, an aperture through the substrate, and a thin, annular metallic ring surrounding the aperture on the opposing surface of the substrate, with the aperture having a diameter less than the wavelength of the incident light.
Figure 11:
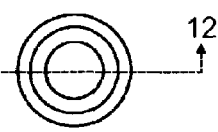
FIG. 11 is a view illustrating the approximate size of the circular area illuminated by the light transmitted through the aperture in the structure shown in FIG. 10.
Figure 12:
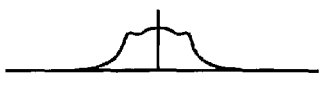
FIG. 12 is a graph illustrating the illumination intensity in the illuminated area taken along the line 11-11 of FIG. 10.

A third structure that may be used as a source of concentrated light is shown in FIG. 10. As in the structures shown in FIGS. 4 and 7, a thin metallic film 121 covers the upper surface of a dielectric substrate 123. A hole 124 through the film 121 and the substrate 123 is not lined with a conductor as in FIG. 7. Instead, an annular ring 125 of conductive material surrounds the exit end of hole 124 at the lower surface of the substrate 123. The conductive ring 125 increases the coupling with the film 124 to improve light transmission through the hole 124 but does not permit the surface excitations surrounding the hole exit to spread beyond the outer periphery of the ring 125, thereby again achieving the more concentrated, steep skirted output light pattern shown in FIGS. 11 and 12.

Figure 13:
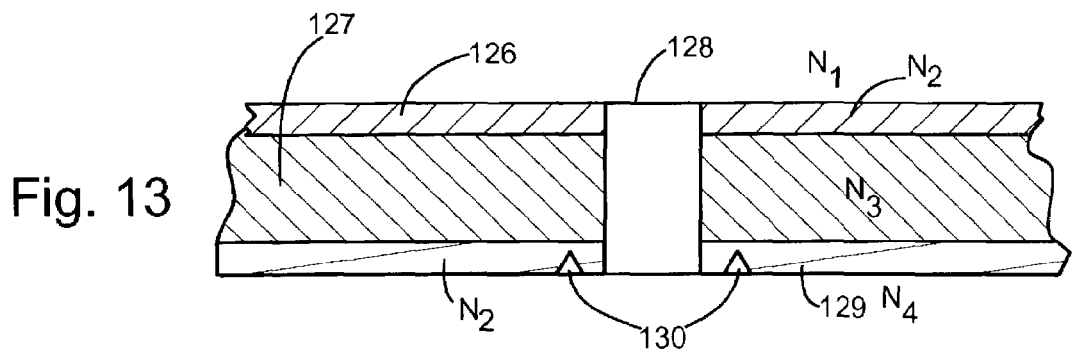
FIG. 13 is a cross-sectional view of a hole structure in which a thin metallic film which covers both surfaces of a non-metallic substrate material, and an annular notch is cut into the film at the exit surface which surrounds and is spaced from the hole.
Figure 14:
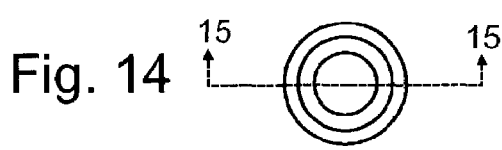
FIG. 14 is a view illustrating the approximate size of the circular area illuminated by the light transmitted through the aperture in the structure shown in FIG. 13.
Figure 15:
FIG. 15 is a graph illustrating the illumination intensity in the illuminated area taken along the line 15-15 of FIG. 14.

FIG. 13 shows still another structure in which a dielectric substrate 127 is coated on its upper surface with a metallic film 126 and on its lower surface with a metallic film 129. The hole 128 passes through both films and through the substrate and its side walls are not coated. An annular groove seen at 130 is formed in the film 129 and surrounds and is spaced from the hole 128. The groove has a nominal outside diameter of 25 nm and inside diameter of 20 nm. The depth of the groove must be at substantially deeper than the skin depth of the material, i.e., deep enough to act as insulator with respect to induced surface excitations. The groove may have any convenient shape and may be rectangular or triangular as well as semi-circular. Note that, by using a groove of the type shown in FIG. 13, an optically thick metallic structure may be used instead of a dielectric substrate, so that the hole is effectively lined by a conductor. In both cases, the groove serves to contain the coupled electron excitation within a surface area close to the hole exit, thereby preventing unwanted spreading of the illumination pattern. The illumination pattern produced by the hole and groove configuration of FIG. 13 is depicted in FIGS. 14 and 15.

Figure 16:
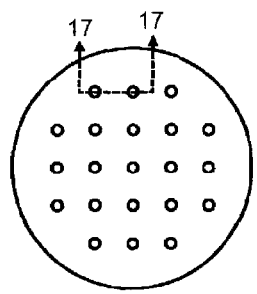
FIG. 16 is an end plan view of a multi-aperture probe constructed in accordance with the invention.
Figure 17:
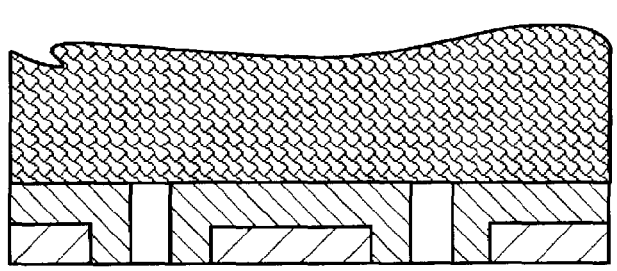
FIG. 17 is a cross sectional view of the probe seen in FIG. 16 take along the line 17-17.
Figure 18:
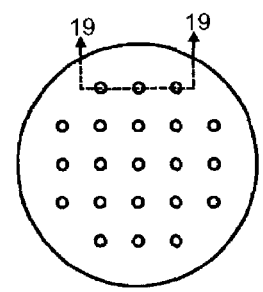
FIG. 18 is an end plan view of an alternative structure for the multi-aperture probe constructed in accordance with the invention.
Figure 19:
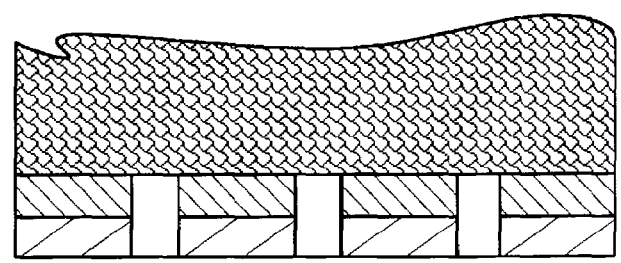
FIG. 19 is a cross sectional view of the probe seen in FIG. 18 taken along the line 19-19.

As will be discussed later in conjunction with FIG. 22, the principles of the invention may be used to construct a multi-aperture probe (MAP) which may be used to advantage in scanning microscope. FIGS. 16 and 17 illustrate a MAP structure using holes with electrically conducting sidewalls of the type discussed earlier in connection with FIGS. 7 and 13, while FIGS. 18 and 19 show the construction of a MAP having holes whose sidewalls are in part non-conducting as previously discussed in connection with FIGS. 4 and 10 of the drawings.

As also discussed above, another approach to eliminating the prolate pattern is to align the polarization with a slit. If the material through which the photons are propagating has low charge availability (as in slit), there can be very few or no surface plasmons. Also, the propagation of light is supported along the slit and throughput should be higher for an array of slits versus an array of circular holes of the same area. Work done on slits much smaller than the transmitted wavelength (32 nm slit) [see Astilean, Lalanne and Palamaru "Light transmission through metallic channels much smaller than the wavelength" *Optics Communications* 175 265-273 March 2000] in optically thick metal films shows peaks in the NIR and visible transmission versus incident wavelength curves with maxima in the order of 80% efficiency for the plate with a grid spacing of 900 nm. For the strongest peak, 1.183 μm, this is an extraordinary amount in that almost 10 times the amount of light impinging on the slits is transmitted through them. Also reported are slits of 10 nm widths, which when excited at resonance, achieve 10% efficiency. Astilean et al. conclude that the resonance condition is not only a function of the SP resonance but that the metallic wall linings of the slits act as Fabry-Pérot cavities and that greatly enhanced transmissions occur when the slit satisfies the Fabry-Pérot resonance condition [see Born, M. and Wolf, E. *Principles of Optics*. Cambridge University Press 6th ed. 1980 p.326] with an effective index of refraction which depends strongly on the slit width and material.

Figure 20:
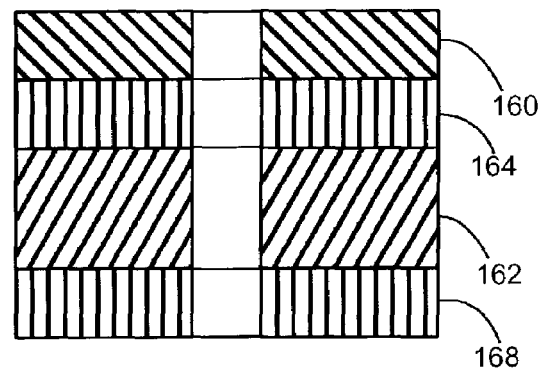
FIG. 20 is a cross sectional view of an alternative light barrier structure employing "good" and "bad" metal layers.

FIG. 20 shows still another configuration which utilizes the principles of the present invention. In this arrangement, the light barrier is composed of three different materials: a "good" metal layer 160 over a substrate consisting of an insulator 162 sandwiched between two layers of "bad metal"

164 and 168. As with the other structures, the "good" metal used in layer 160 is one in which the surface plasmons will decay over a relatively long distance as determined by the surface roughness of the film 160 (which includes the holes) and the relative values of the real and imaginary parts of the dielectric function of film 160 (where a small imaginary part provides a long delay decay length). In contrast, the "bad" metal used in the layers 164 and 168 has a dielectric function with a large imaginary part so that the surface plasmons decay more quickly over a relatively short decay length.

The "bad" metal used in layers 164 and 168 preferably exhibits two additional properties which make a significant contribution to the creation of nanometric light sources. First, the "bad metal" should be opaque to the light emitted from the surface of the "good" metal in thin films. Second, the resonance of the "bad" metal layer(s) should be should be very different than that of the "good" metal. The resonance of the metal layers is determined only by the real part of the dielectric function for metal, the surface roughness of the metal layers, and the dielectric functions of the materials on either side of the metal layer.

The insulator 162 ensures that there can be no surface plasmon communication from top to bottom through bulk plasmons or any other direct electronic interaction. Note, however, that the presence of the insulator 162 may not required if the bad metal satisfies the criteria expressed above; that is, is opaque to light emitted from the good metal layer and has a resonance that is very different from the good metal layer.

For the all of the structures described in connection with FIGS. 4-20, the diameter of the hole should be between about 2 nm and 50 nm. The metallic film layers should, as noted earlier, be at least skin depth of the electronic excitation and may be formed, for example, from gold, silver, aluminum, beryllium, rhenium, osmium, potassium, rubidium, cesium, rhenium oxide, tungsten oxide, copper or titanium (if employed at the appropriate frequencies). Suitable dielectric and "bad metal" substrate materials include germanium, silicon dioxide, silicon nitride, alumina, chromia, some forms of carbon and many other materials including some of the metals listed as "good metals" at the appropriate frequencies. The aperture array with sub-wavelength holes may be fabricated using available focused ion beam (FIB) milling techniques.

The physical structures for producing very small spot and slit illumination may be used to advantage in a number of different applications as next described.

Optical Data Storage Using Small Spot Illumination

Figure 21:
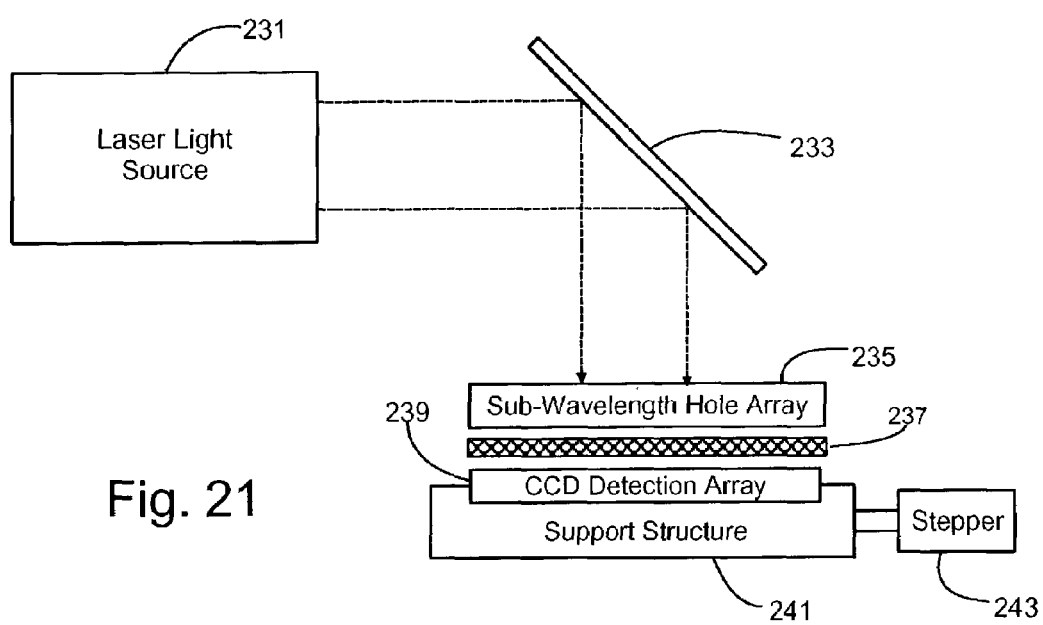
FIG. 21 is a schematic diagram of a data storage device that uses an array of nanometric holes to illuminate a data storage array as contemplated by the invention.

FIG. 21 illustrates the manner in which a nanometric light source array of the type contemplated by the invention may be used to increase the storage density in an optical storage device. The optical memory consists of a light source 231, such a solid state NIR laser as shown in FIG. 21. The light from the source 231 is directed onto the metallic film surface of a nanometric hole array 235 using a fold mirror 233. The nanometric hole array 235 collects and funnels the light such that an array of discrete areas of illumination are directed toward the optical storage medium 237. At each area of illumination, a data value stored at that location in the storage medium controls the intensity of the light which passes to a pixel location on a charge coupled device array (CCD) 239 and hence controls the output data value from that CCD pixel. The holes in the array 239, the data storage regions in the medium 237, and the pixel locations in the CCD 239 are equally spaced so that they are properly aligned. A translation mechanism effects movement of the storage medium relative to the hole array in incremental steps, with each step distance being equal to the aperture size.

In the year 2000, commercially available CCD arrays have pixel sizes no smaller than $(4\ \mu m)^2$. If this is a limiting case, optics between the storage medium and the CCD array could be used to allow less movement. The step size would then be down to that demanded by the Rayleigh criterion.

Note also that the amount of data stored at each pixel location may be increased by storing more than two signal levels; for example, gray scale or color values may be stored as analog signal magnitudes at each storage location.

Figure 35:
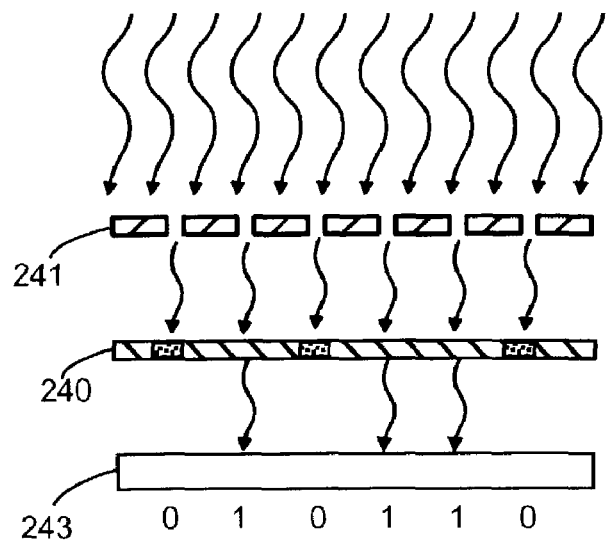
FIG. 35 is a schematic diagram of an arrangement for reading data from a data storage medium.

The data reading technique employed in the optical data storage system is illustrated in FIG. 35. The optical medium 240 is illuminated by the spot illumination from the SPEI array 241 and the light transmission through the medium 240 is read by the radiation detector 243 which may take the form of a charge coupled device (CCD) array, a complementary metal oxide semiconductor (CMOS) array, or other array of radiation sensing elements which senses the previously written state of the optical storage medium at each pixel location.

Figure 36:
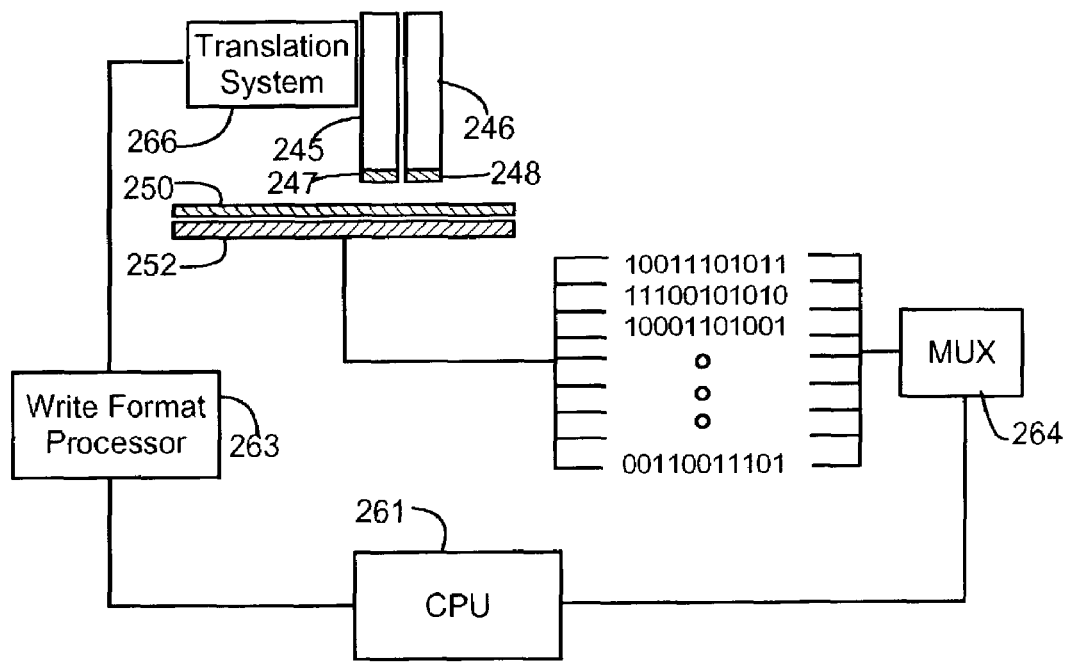
FIG. 36 is a schematic diagram of a further embodiment of a data storage system employing the invention.

An alternative optical data storage system using SPEI is shown below in FIG. 36. The system employs semiconductor lasers seen at 245 and 246. The laser 245 is fitted with a write mask 247 and the laser 246 is fitted with a read mask. Both masks are SPEI arrays that provide approximately 10,000 apertures each 10-50 nanometers in diameter. The optical medium seen at 250 rotates or otherwise moves with respect to the CCD or CMOS detector array seen at 252. The detector array 252 may be a 100×100 read array, or larger, to provide fast data access. Operating under the control of a CPU 261, a write format processor 263 accepts data to be stored and drives a translation system 266 which moves the write head comprising the laser 245 and the write mask 247. When the data is read from the storage unit, it is collected in parallel by the detector array 252, multiplexed at 264 and returned to the CPU 261.

Figure 23:
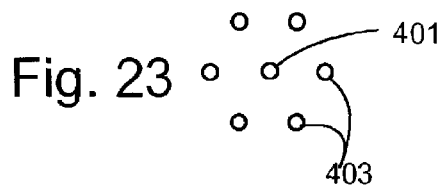
FIGS. 23-24 is a plan view of the location of surface patterns surrounding a central aperture used to enhance the illumination from the central aperture.
Figure 24:
Figure 34:
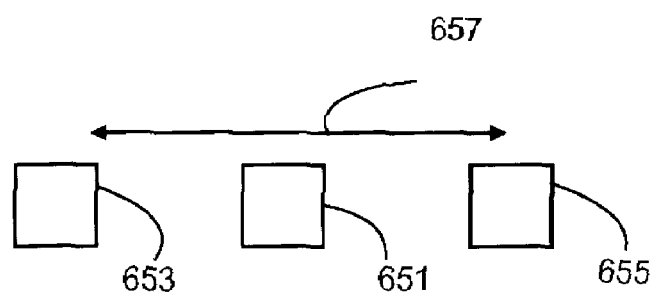
FIG. 34 is a plan view of the location of a central square hole and surrounding square surface irregularities that may be employed for greater packing density.

To achieve a rugged, compact system, the SPEI mask (247 or 248) may be fabricated onto the semiconductor or LED light source (245 or 246). The write head (laser 245 and mask 247) may be performed in parallel, but at a different level of parallelism as is achieved in reading. It requires a higher illumination intensity to write data into the optical medium 250 than to read previously stored data due to the need to produce the photochemical change required for writing at an adequate rate. To achieve that increased intensity, the SPEI is modified in the manner discussed below in connection with FIGS. 23, 24 and 34. For writing all, only selected central apertures pass through the SPEI array. At positions surrounding each central aperture, areas of surface roughness (dimples) deeper than the skin depth of the good metal are positioned as shown in FIGS. 23 and 34, or the central aperture is surrounded by an annular groove as shown in FIG. 24. This technique allows the extraordinary transmission to be retained while only providing emission from the central aperture. This central aperture then becomes the scanned element that is used to write to the medium. This writing feature can also be used for reading.

Two factors determine the data packing density that can be attained using SPEI data storage: the size of the apertures and the light transmission fraction achieved.

Cylindrical holes produced using a focused ion beam (FIB) are typically limited to an aspect ratio of 5-6:1 for the depth versus diameter. Accordingly, for a read or write mask having a thickness is 275 nm, the minimum aperture diameter is approximately 55 nm. By using thinner $Si_3N_4$ membranes and pushing the limits of the FIB, the ultimate limit is believed to be in the vicinity of 10 nm. Devices have been fabricated on 150 nm thick silicon nitride membranes. For smaller apertures, still thinner membranes may be substituted, or the membrane completely may be completely eliminated. Moreover, the holes need not be cylindrical and may be tapered and still provide high light transmission.

The light transmission fraction is expected to be proportional to the aperture diameter to the first power. "Shutters" may be placed between the light source (the laser 245) and the SPEI device (the write mask 247) to provide parallelism for the write function. The minimum shutter size may limit the density of emitting apertures. The emission from selected portions of the SPEI device may be performed using an LCD (not shown (to block the light, or the local dielectric function at the interface may be alerted as demonstrated by Kim et al. in the paper "Control of optical transmission through metals perforated with sub wavelength hole arrays," Opt. Lett. 24, 256-258 (1999). In still another shuttering method, conductive wires may be attached to influence the individual resonant patterns in the device and, thereby, alter the electron density and the resonance of the surface plasmons in the area local to selected aperture in question, thereby modulating the aperture's emission pattern.

The use of SPEI to implement optical data storage systems possesses numerous important advantages. Using the techniques described above, it is believed that data storage devices capable of storing 2.8 Terabit/in$^2$ (with 10 nm apertures and with the data stored in a binary format) can be fabricated. SPEI arrays with 50 nm (82 Gigabits/in$^2$) apertures have been constructed, and aperture sizes as small as 2 nm are possible to potentially yielding 70 Tb/in$^2$ storage densities. As noted earlier, Gray scale or color recording offers the potential for further increases in data density. Data may be read from the device in massively parallel format, achieving read rates that exceed 1500× those for CD technology. High light transmission fractions (15.3% of the light incident on apertures (50 nm) is transmitted in propagating modes to the optical medium) have been achieved in very early devices of SPIE architecture. Because the light is propagating, sub wavelength illumination may be achieved without resorting to near-field techniques. A wide range of illuminating wavelengths may be employed, ranging from the deep ultraviolet to infrared, which permits the selection of a wavelength to optimize the performance of the photochemical used as the optical storage medium. The high light transmission fraction combined with flexibility in the wavelength of the light delivered provide the photochemist with the possibility of either using existing chemistries or creating new formulations to take advantage of the properties of light emitted from SPEI devices. The system operates in ambient environments (no cryogenic temperatures or vacuum are required for operation). SPEI data storage is compatible with a broad range of applications to meet the needs of large data centers, high density backup system, and storage for desktop and handheld devices. Unlike magnetic technologies, data stored in a SPEI medium is immune to electromagnetic impulse.

Surface Plasmon Enhanced Microscopy

Figure 22:
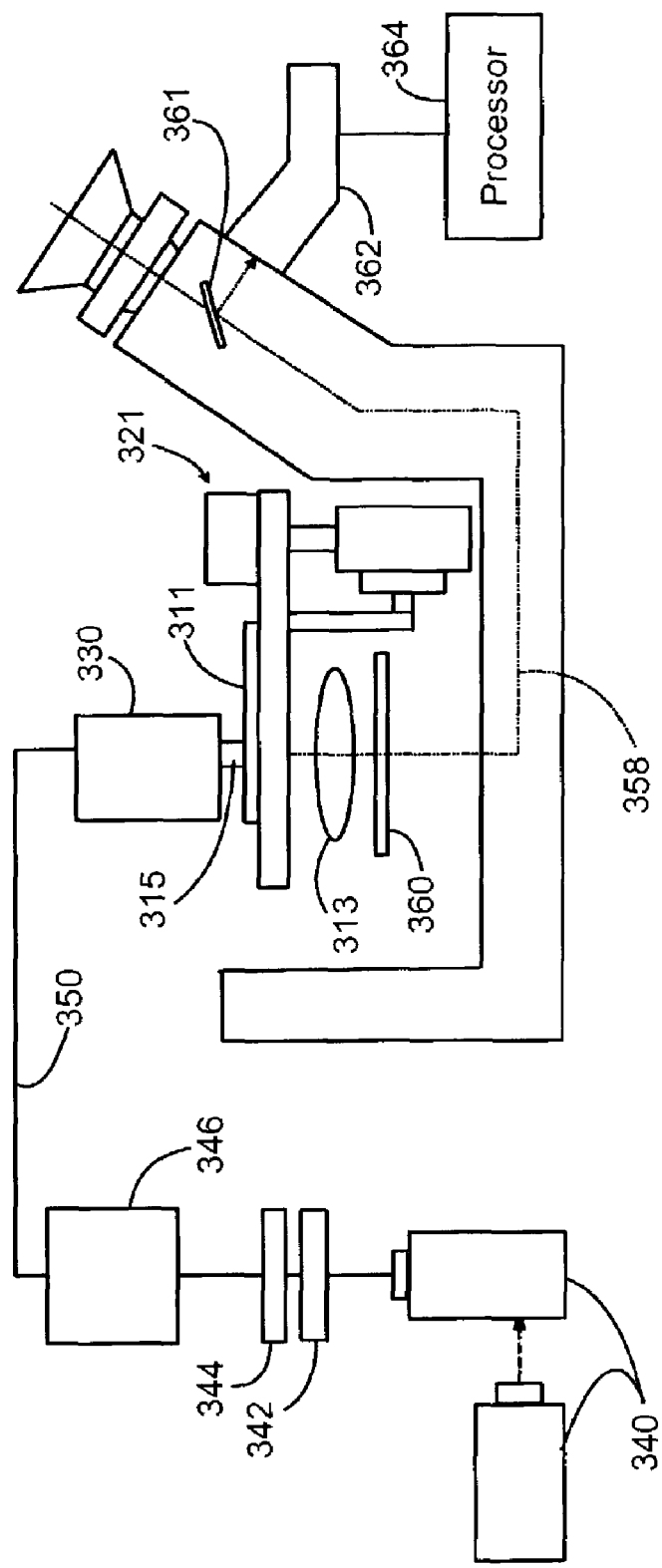
FIG. 22 is a schematic diagram of a Surface Plasmon Enhanced Microscope (SPEM) which embodies the invention.

FIG. 22 of the drawings illustrates the use of the nanosecond light source array as contemplated by the invention to construct a "Surface Plasmon Enhanced Microscope" SPEM). A sample 311 is placed between the objective lens 313 of the microscope and the multi-aperture probe (MAP) 315. The sample is mounted on a transparent, flat substrate placed on a translation stage 321 capable of nanometric movement. The MAP 315 is then moved into close proximity to the sample 311 and held in place by a compressive force module or proximity sensor 330. In fluorescence mode, light is emitted by a light source, such as a pumped laser, a light emitting diode, an arc lamp or other white light generator, 340 and transmitted via neutral density filters 342, polarizers 344, a fiber coupler 346 and an optical fiber 350 down to its terminus at the MAP 315, where it is emitted through an array of holes in a mask that has been fabricated onto the end of the optical fiber. The light leaving the holes strikes the sample 311 at its surface. The far field light path 358 from the objective 313 passes through a low pass filter 360 to a beam splitter or mirrored shutter at 361 which redirects the light to a array charge coupled device (CCD) 362 that converts the light into electrical signals which are passed to the processor 364 which performs image capture (frame grabbing) and other image processing functions.

In fluorescence mode, the impinging light is absorbed by fluorophores, which resonate, emitting photons at a different frequency. The fluorescent light is collected in the far field by the objective lens and then transmitted into oculars 370 or to the data collection device (e.g., the CCD array 362.)

Once the entire sample has been illuminated by the array of apertures, the resulting fluorescence is collected in the far-field. The MAP 315 is then raised and the sample 311, or the MAP, is indexed to the next position and another set of measurements is made. This process is repeated until the space between the spots, 250 nm to 600 nm, has been scanned. This is a much easier and faster task than with NSOM. In an alternative arrangement the MAP is simply scanned and the raising and lowering steps are eliminated.

It should be clear from the above discussion that it would be difficult to design a probe of the types above with the aim of efficiently transmitting a multiple of wavelengths chosen to maximize the excitation of a suite of fluorophores. One solution is to make tunable MAPs by dynamically modifying the effective dielectric function of the secondary metal (the metal probably would be replaced by a semiconductor) during operation. By changing the dielectric function of the surface below the primary metal, the frequency of emission can be changed substantially. [See Kim, T. J., Thio, T., Ebbesen, T. W., Grupp, D. E. & Lezec, H. J. Control of optical transmission through metals perforated with sub-wavelength hole arrays."Opt. Lett. 24, 256-258 (1999) using a twisted-nematic liquid crystal under an array]. It has also been shown that the application of a magnetic field has strong effects on the dielectric function [see Strelniker, Y. M. & Bergman, D. "Optical transmission through metal films with a subwavelength hole array in the presence of a magnetic field." Phys. Rev. B 59, 12763-12766 (1999). Another method of tuning the array may be to have domains surrounding the apertures in which the density of electrons can be modified by passing an electric current through that domain. The small capacitance of the domain would affect the density of the electrons and, hence, the resonance of the surface plasmons.

Multiple MAPs could be constructed with parameters tailored to each fluorophore of the chosen suite. Each probe would be interfaced to the sample and would present a roughly monochromatic source. As the widths of the peaks of the resonances of the MAPs will be broad (about 20 nm FWHM), the fluorophores will have to be chosen well with significant distances between their excitement wavelengths. In this case, the SPEM will probably be limited to only a few (maybe 6 or so) different fluorophores. However, the quantum dot offers great promise. Bruchez et al. ["Semiconductor Nanocrystals as Fluorescent Biological Labels" *Science* 281 1998.] have successfully used quantum dots as biological markers. Importantly, the quantum dots may be excited by a single source and to be multiplexed such that multitudes of dots can be detected and identified simultaneously.

SPEM has been conceived with clinical and basic research applications in mind and the user interactions have been structured to make it an easy technique to use. The basic steps, for both clinical and basic research use, are:

1. Prepare the sample
2. Select the cells of interest from the slide
3. SPEM automatically captures the data
4. Review the results and generate specific database analyses.

Step 1. Prepare the Sample: In the clinical application the only additional sample preparation step required is to add the antibody-label reagent to the slide and incubate. The tissue sample preparation steps currently in use for pathology slides are done prior to adding the SPEM labeling reagents (antibody-fluor complexes). Generally for cell culture samples the cells will be embedded in paraffin and then treated as tissue samples for the purposes of preparing them for analysis in SPEM. It would be possible, though, by using an actively cooled, transparent, thermally conductive substrate, to investigate frozen tissue samples and, under suitable conditions, it should be possible to study live cells using SPEM.

Step 2. Select the cells of interest from the slide: With SPEM the user looks at the slides with a standard far-field microscope prior to the high resolution investigation. This allows the user to make use of the morphology data available today and select cells for further analysis that are the most interesting. To accomplish this, the SPEM system will incorporate a module that allows the user to digitally mark (record the x-y coordinates) the cells for further analysis. This allows the user to gather data on different cell types, cells at different stages of the cell cycle, and multiple cells of the same type to increase the statistical power of the near-field analysis. This also should allow the user to create multiple slides from the same cell representing sequential cuts from the microtome. The resulting SPEM data can then be reconstructed to create a three dimensional data set of protein locations and expression.

Step 3. SPEM automatically captures the data: The SPEM system will execute the illumination and far-field collection steps described above to generate a database of protein localization and expression information.

Step 4. Review the results and generate specific database analyses: The database created in the previous step provides the user with the ability to create custom queries to address the biological or clinical question under investigation. It is expected that as SPEM matures there would be a library of specific database queries that would be used. In particular, for clinical use pathologists would have a set of standard analyses that are performed with the SPEM to elucidate molecular signatures of cancer.

SPEM generates a data file consisting of the location of every fluor detected in the cell, and the protein with which it is associated. This data file can be analyzed in a number of ways, including:

i) Generating a map of each protein's location within the cell that is superimposed on an image of the cell.
ii) Providing the number of copies of each protein that were detected.
iii) Statistics for a number of conditions:
  (a) Percentage of copies in the nucleus or cytoplasm
  (b) Number of copies of a protein that are within a user specified distance of either another protein, or a cellular feature (e.g. cell membrane)
  (c) Comparisons between cells (e.g. mutant and wild type)
  (d) Comparisons of protein locations and expression levels between cells at different stages of the cell cycle.
  (e) Comparisons between cells at different developmental levels
iv) Assist in the selection of therapies and determination of prognoses for cancer patients based on molecular signatures of cancers.

The strengths of SPEM include:
(1) The ability to obtain protein localization and expression data for multiple proteins in a cell from either cell culture or a tissue sample.
(2) Localization resolution better than 75 nm, and possibly as low as 10 nm.
(3) Protein expression data based on protein levels, not on mRNA.
(4) Permits the study of low copy number proteins.
(5) Less sensitive to vibrations than NSOM and Atomic Force Microscopy. The level of vibration isolation that is needed is similar to standard microscopy techniques.

The MAP used in a SPEM should:
(1) Have an array 75 nm (or smaller) holes that can illuminate a tissue sample with enough energy to excite fluors that have been bound to specific proteins in the sample.
(2) Have a diameter of at least 20 µm in order to cover a typical cell.
(3) Have the holes in the array spaced far enough apart to permit collection of optical data from the fluors using far-field optics (greater than the distance imposed by the Rayleigh criterion for the objective lens being used for collection and the emission wavelength of the lowest frequency fluorophore.)
(4) Maintain high resolution registration of the locations of the holes in the array relative to the far-field optics.
(5) Have optical and thermal conductances that are high enough to avoid deteriorating levels of thermal expansion of the MAP and heating of the sample.

Fabrication of the MAP should be undertaken with the following parameters in mind: the ability to control aperture size (geometry and thickness); the ability to control aperture spacing; the nature of the materials (e.g. purity, continuity); and the characteristics of the coating needed (e.g. continuity and thickness).

In the metal film experiments above, the holes in the films were created by two methods, both achieving excellent cylindrical geometry. In the Sönnichsen experiments, a suspension of polystyrene beads was spin-cast onto a very thin (1 nm) adhesive layer on a glass substrate and a subsequent metal film evaporated onto the adhesive and the spheres. The spheres and the metal covering them were then removed by ultrasonification. In the experiments conducted by NEC Research, the holes were created by focused ion beam milling (FIB). This method allowed more latitude in the hole size and spacing in the metal film.

Because the preferred structures are both heterogeneous and require that the hole spacing is uniform (for scanning purposes) or at least well characterized and repeatable from MAP to MAP, the method of spin casting is not useful. FIB can be used but may be expensive for the use of SPEM in clinical settings. Another proposed method of fabrication is to use a naturally occurring structure of alumina. Alumina can be anodically etched to produce a uniform nanometric, closely packed honeycomb structure over large areas [see Keller et al. *J. Electrochem. Soc.* 100 411 1953, Thompson et al. *Nature* 272 433 1978] By using micromanipulation, holes could be filled with an insulator or conductor leaving only apertures where desired. The structure would then be coated with the chosen electrical conductor and the bottom surface milled away using FIB.

The SPEM microscope illustrated in FIG. 22 may be implemented using commercially available components. An inverted fluorescence microscope such as a Zeiss IM35 or a model from the Zeiss Axiovert family would be suitable for modification. The microscope should have at minimum, two high numerical aperture (1.3 or greater) Plan-Apochromat objectives; one for high magnification (100×) and one for medium magnification (63×.) Because the exciting photons are traveling in the MAP, and there is no ultraviolet light involved, special glasses and coatings are not required. The above objectives have been corrected at the red, green and blue wavelengths for chromatic aberration and will, hence, not be a problem with different fluorescing colors.

At low levels of fluorescence (low light input is desired to minimize the effects of photobleaching and possibly, with two-photon excitation, stimulated emission depletion) that may be seen in the SPEM, cooling is required when using a charge coupled device (CCD) array to maximize signal to noise ratio. Zeiss manufactures a suitable high resolution (1300×1030 pixels) thermoelectrically cooled CCD array/frame grabber package called Axiocam with color density of 14 bit color classification which is adequate for purposes of multiple fluorescence capture and discrimination. The Axiocam is sold by the Microscope Division of Carl Zeiss with software called AxioVision that is supplied along with the CCD array, a thermoelectric cooler, frame grabber and image analysis software that are integrated with and designed specifically to mate to the Axio microscopes.

Translation of the sample relative to the MAP and collection optics requires a 3 axis translation stage shown generally at 321 in FIG. 22. The step size of the translation stage and its resolution should be less than the required resolution desired of the spatial resolution of fluorophores in the sample. Mad City Labs (Madison, Wis.) offers such a device called the Nanobio350. The controller is delivered with LabView software to make integration with the imaging system easier.

Although the above-noted CCD array is color sensitive and discriminating, it is sensitive into the wavelength regime (NIR) of the emission laser. So that the pixels are not saturated with the stimulating radiation and to avoid more computation than necessary, an optical low pass filter should be placed in the path between the CCD input and the objective lens of the microscope. There are numerous suppliers for such filters. If a laser light source is used, a grating compensation system may need to be employed to avoid the dispersion that would otherwise occur in the fiber. These are available from Coherent.

The current factor that limits the number of proteins that can be simultaneously characterized using SPEM is the limited availability of spectrally distinguishable fluorophores. Many researchers are working on this issue and it is expected that SPEM will benefit greatly from these efforts. Some of the more interesting candidates are described below.

Because the MAP will be designed for efficient transmission of one specific wavelength of light, a set of fluorophores that can all be excited by the same wavelength will need to be selected. There are two promising methods for this: 1) two-photon excitation of fluorescent dyes, using an infrared light source, and 2) quantum dots, using a blue-violet light source. For fluorescent dyes, we would need a set with well-separated emission wavelengths and narrow spectral peaks. At least two vendors offer products that meet these criteria: Molecular Probes of Eugene, Oreg. offers a set of seven BODIPY dyes, and Amersham Pharmacia Biotech (www.aipbiotech.com) offers a set of five Cy dyes. In addition, new dyes are introduced frequently. Quantum dots are not yet commercially available for biochemical labeling, but are expected to be in the near future. By tailoring the size of the cavity, quantum dots can be made with any desired emission wavelength, so conceivably more than seven could be used within the visible-light spectrum. However, quantum dots are significantly larger than fluorescent dye molecules, 10-20 nm vs. 1-1.4 nm effective diameter. This makes fluorescent dyes the more attractive option. However, if two-photon excitation overheats the SPEM probe, quantum dots will be used for the multiple-labeling experiments.

Quantum dots are nanometer size semiconductor particles with sub-wavelength size pits grown or machined into them. The dimension of the pit determines the color of light emitted from a quantum dot. The pits have dimensions 2 nm (for green light) to 5 nm (for red light), and the overall particle has a dimension of 10-20 nm. It should be easier to develop new quantum dots with precisely tuned emission wavelengths (compared to developing a new fluorophore) by tailoring the exact dimensions of the pits in the quantum dots. Quantum dots have a narrow spectral peak width, with a full width at half maximum (FWHM) of 30-35 nm [see M. Bruchez Jr., M. Moronne, P. Gin, S. Weiss, and A. P. Alivisatos, "Semiconductor nanocrystals as Fluorescent Biological Labels", *Science*, 281, 25 Sep. 1998, p. 2013-2016.]. This is comparable to the seven Molecular Probes BODIPY fluorescent dyes, which have spectral peak widths of 22-35 nm FWHM [FIG. 1.2 of Molecular Probes CD handbook]. Narrow spectral peak widths allow many colors to be distinguished, allowing many reporters to be used simultaneously.

In addition to fluorescent dyes, and quantum dots mentioned above, other types of reporters are also in development. Multiplexing arrangements, which allow a more complex code in each reporter tag, are also in development.

At present, all of these approaches produce tags that are too large. Nanobarcodes (10-20 nm diameter×30 nm long) consist of chips with stripes of reflective gold, silver, and platinum metal. The width and spacing of the lines can be altered. Colloidal particles have been used to tag beads for combinatorial synthesis [see Battersby B J, Bryant D, Meutermans W, Matthews D, Smythe M L, Trau M, Toward Larger Chemical Libraries: "Encoding with Fluorescent Colloids in Combinatorial Chemistry", *Journal of the American Chemical Society*, 122: (9) 2138-2139, Mar. 8, 2000]. In this scheme, a 100-micron diameter bead holds multiple 1-micron diameter colloidal particles. Each type of colloidal particle holds a unique combination of fluorescent dyes. PEBBLE (Probe Encapsulated By Biologically Localized Embedding) sensors consist of fluorescent dyes encapsulated in a polymer matrix; these particles can be as small as 20 nm. While these have been used for sensing ion concentrations in cells [see 1 Clark, Heather A; Hoyer, Marion; Philbert, Martin A; Kopelman, Raoul, "Optical Nanosensors for Chemical Analysis inside Single Living Cells. 1. Fabrication, Characterization, and Methods for Intracellular Delivery of PEBBLE Sensors", *Analytical Chemistry*, 1999, v.71, n.21, pp.4831-4836; and Clark, Heather A; Kopelman, Raoul; Tjalkens, Ron; Philbert, Martin A, "Optical Nanosensors for Chemical Analysis inside Single living Cells. 2. Sensors for pH and Calcium and the Intracellular Application of PEBBLE Sensors", *Analytical Chemistry*, 1999, v.71, n.21, pp.4837-4843], the technique may be extendable to labeling proteins.

It is possible that the light output from the holes in the MAP will cause illumination of fluorophores or quantum dots in planes substantially below the surface over which the MAP sits. These molecules could be excited by the spreading photons and may, therefore, not be directly in line with the axis of the holes but could be in between the axes of several holes resulting in a weak magnitude positive signal at more than one location, yielding incorrect spatial information and possibly concentration or color. Methods to reduce this misinformation could be (but certainly aren't limited) to making the tissue sample or the image sample as thin as possible or using multi photon excitement. Because of the squared dependence of the two photon excitement of location, there will be a substantially higher chance of two photons arriving concurrently directly in line with the axes of the holes than anywhere else below the MAP, potentially enhancing resolution.

Other modifications to the MAP may be implemented to modify the resonant wavelengths. One method would be to change the in-plane magnetic field of the MAP. It has been shown the direction and the magnitude of the field can dramatically affect the resonant wavelengths by affecting the effective dielectric functions of the metals. Another method may be to change the density of electrons in the metals to also affect the effective dielectric functions. This could be achieved in numerous fashions. The simplest would be simply to "pump" electrons into the metal. Possibly, localization of charges and/or magnetic fields could allow the MAP to perform read and write operations in storage media and could be used a polychromatic excitation source for fluorophores.

High Resolution, High Throughput Photolithography

The ability to create spots of light with diameters that are well below the wavelength of the light forms the basis of a new approach to lithography and photochemistry. The array structures described above can be modified in a very simple way to achieve a useful tool for lithography. In the structures discussed in connection with FIGS. 4-20 above, all of the apertures in the array penetrate the SPEI light barrier and as a result all emit light. For lithography, all but the central aperture in a set (the smallest number of apertures required to establish the resonant condition) would be changed from apertures that go through the barrier to elements of surface roughness (dimples or protuberances) that are deeper than the skin depth and the same diameter as the aperture. Alternatively, the dimples surrounding the central aperture can be replaced with an annular groove or raised ring having a width equal to the emitting hole diameter and a depth greater than skin depth. This technique allows the extraordinary transmission to be retained while only providing emission from the central aperture. This central aperture then becomes the scanned element that is used to write to the photoresist to perform lithography.

This structure is shown schematically in FIGS. 23 and 24. FIG. 23 illustrates a hexagonal pattern of apertures (one emitting aperture 401 surrounded by six dimples 403) where the relationship between the resonant wavelength and the spacing is governed by the first equation below. Other lattices are permissible with similar equations in which the integer indices (i and j in the equations below) are modified for the specific lattice type (for example a circularly symmetric lattice (central hole surrounded by annuli)) would be governed by the second below equation where $\rho$ is the radius of $1^{st}$ annulus and i is an integer describing the number of annuli away from the center. The third equation is for a square array. For a linear array, j is zero.

$$\lambda_{max} = a_0 (4/3(i^2 + ij + j^2)^{-1/2} \left(\frac{\varepsilon_1 \varepsilon_2}{\varepsilon_1 + \varepsilon_2}\right)^{1/2}$$

$$\lambda_{max} = \rho \Big/ i \left(\frac{\varepsilon_1 \varepsilon_2}{\varepsilon_1 + \varepsilon_2}\right)^{1/2}$$

$$\lambda_{max} = a_0 (i^2 + j^2)^{-1/2} \left(\frac{\varepsilon_1 \varepsilon_2}{\varepsilon_1 + \varepsilon_2}\right)^{1/2}$$

where: $\lambda$ is the wavelength, $\epsilon_1$ and $\epsilon_2$ are the real portions of the dielectric constants for the metal and the surrounding medium, $a_0$ is the lattice constant (spacing between dimples/apertures), while i and j are integers characterizing the particular branch of the surface plasmon dispersion. See Raether, Heinz "Surface Plasmons on Smooth and Rough Surfaces and on Gratings" Springer Tracts in Modern Physics v. 111, Springer-Verlag, Berlin 1988.

FIG. 24 shows an alternative arrangement in which the single emitting aperture 407 is surrounded by an annular groove 409 with a width equal to the diameter of the emitting hole. In accordance with the invention, means are employed for limiting the extent of surface plasmon excitation at the exit surface of the emitting hole to the hole itself, or to a small area surrounding the rim of the hole at its exit, thereby confining the area of illumination to achieve higher resolution. All of the light barrier configurations described above in connection with FIGS. 4-20 may be employed to limit the illumination area produced by the emitting hole.

The optical system required to execute SPEI lithography is very simple; there are no reduction lenses or steering mirrors. All that is required is a somewhat monochromatic light source, such as a filtered broadband (e.g. Hg lamp) source or a laser, the SPEI device, a subnanometer translation stage (e.g. the nanopositioning systems available from Mad City Labs, Inc. of Madison, Wis.), a proximity sensor to maintain the SPEI device at a proper photoresist distance, and a photoresist coated wafer.

Three techniques may be used to improve the throughput of the SPEI lithographic process. First, a SPEI device is used to achieve high light transmission in order to increase the speed at which the photoresist can be patterned. The other two approaches increase the parallelism of the writing operation as described below.

The first level of parallelism is achieved by the creation of a SPEI array that contains one emitting aperture for each IC on a wafer. The spacing between emitting apertures will be the same as the spacing between ICs on the wafer. By doing this, the same pattern can be written to all ICs at the same time. To achieve a level of stiffness that maintains the flatness of the device and therefore achieves a uniform device-to-photoresist spacing, a transmissive substrate may be prepared using the same techniques used to prepare semiconductor wafers and fabricate the SPEI device on the wafer. The SPEI device should match the index of refraction of the glass instead of air. The resulting wafer/SPEI device should be rigid enough to allow for a constant CD to be maintained; otherwise, the SPEI device would have to be farther from the photoresist and divergence of the emitted light will increase the minimum CD that can be achieved. If the device is not rigid enough we expect to fabricate structural elements into it to achieve the desired stiffness. The light source should provide uniform illumination over the wafer diameter.

The second level of parallelism is achieved by writing multiple features within an IC in parallel. This is achieved with two modifications to the system. First, "shutters" are added between the light source and the SPEI device. Second, an SPEI device is constructed that has provides a palette of different shapes. The two basic shapes that would be included are a circular (or square) aperture and a line segment. Each of these shapes is preferably provided in different sizes (diameters for the circular apertures, and lengths and widths for the line segments), and the line segments preferably have different orientations (horizontal, vertical, +/−45°).

The minimum shutter size will be the consideration that drives the density of emitting apertures. Shuttering the emission from portions of the device may be performed using a liquid crystal device to block the light or locally affect the dielectric function of the good metal or by attaching wires to the individual resonant patterns in the device to alter the electron density and, hence, the resonance of the surface plasmons in the area local to the aperture in question, thereby controlling a pattern's emission.

By using the invention to create small illumination spot sizes, lithography employing surface plasmon enhanced illumination provides numerous advantages, including:
  a) small spot size (2-50 nm) for enhanced resolution;
  b) high throughput coupled with high resolution, making it particularly useful for semiconductor fabrication;
  c) high light transmission;
  d) no diffraction problems with masks as the critical dimensions and CDs are reduced
  e) more flexible range the light wavelengths can be used, delivering high resolution light over a broad range of wavelengths (from deep ultraviolet well into the infrared range, supporting development of new photoresist chemistries for a variety of applications.
  f) maskless production technology is compatible with rapid prototyping and low production volumes as well as high volume runs;
  g) the cost and complexity of SPEI lithography are compatible with creation of a system that can be used for rapid prototyping of semiconductors, creation of high-resolution masks for e-beam and extreme UV, and other research uses of photolithography;
  h) provides a general purpose tool to be used in non-semiconductor lithography applications in the fields of biology, drug discovery, and clinical diagnostics, including lithography applications such as biosensors, bio-patterning, and array detectors (DNA microarrays, protein and small molecule arrays), all of which that benefit greatly because SPEI can deliver small critical dimensions (CDs) without resorting to ultraviolet light that damages bio-molecules ; and
  i) further lithography applications such as MEMS, self-assembly, molecular electronics, and the study of physics phenomena at very small dimensions.

SPEI photolithography may be employed as a manufacturing method for a binding biosensor or nucleic acid microarray in which the density of nucleic acid probes substantially exceeds the density that can be achieved using traditional photolithography methods that are limited by the Rayleigh criterion. SPEI lithography can also be used for any type of array sensor where photochemistry is used to prepare the surface for immobilization of a ligand or in situ synthesis of the ligands. For example, in very large scale immobilized polymer synthesis systems, a substrate having positionally defined oligonucleotide probes is synthesized. See, for example, Pirrung et al. U.S. Pat. Nos. 6,416,952; 5,143,854; and 5,489,678. In these prior arrangements, conventional projection photolithography using masks with UV illumination is used in combination with photosensitive synthetic subunits for the stepwise synthesis of polymers according to a positionally defined matrix pattern. Each oligonucleotide probe is thereby synthesized at known and defined positional locations on the substrate. However, the density of the array is constrained by the conventional photolithography methods whose resolution is limited by the Rayliegh criterion. By using SPEI, this synthesis process may be performed using a direct write method, eliminating the need to create a mask, and providing significantly improved probe density. Direct write is the equivalent of using a paint brush to paint a picture whereas projection lithography with masks is akin to silk screening the picture. Silk screening, when it is compatible with the resolution required is faster. However, the masks in photolithography are expensive and they wear out. This will increasingly be a serious problem for the semiconductor industry as the feature sizes decrease the cost of the masks increase and their lifetime decrease.

It will be apparent to one skilled in the art that the use of the invention for photolithography extends to all photochemical applications where a pattern is created, as photolithography is a specific field of photochemistry. This would include the preparation of surfaces for subsequent operations and/or chemical reactions, or the creation of micro- or nano-reaction vessels in which the chemical reaction is caused or promoted or inhibited by the addition of light.

SPEI Applied to Genomics and Systems Biology

Functional genomics and systems biology are fields that address gene function on tissue or organ system specific bases by studying the complex interactions between proteins, RNA, and DNA and other biomolecules present in cells and extracellular spaces. To accomplish this, macromolecules need to be studied in complex mixtures that replicate the in vivo environment as closely as possible. The enormity of the task calls for analytical methods that can be scaled to operate combinatorially, thereby allowing for a genomic scale approach to the problem. Furthermore, due to the statistical nature of many macromolecular interactions, it is important to have the ability to study them at the single molecule level to avoid the loss of information resulting from ensemble averaging. This is particularly important in situations with bimodal distributions where the average is not representative of any of the molecules' states. This also imposes the requirement that statistically significant sample sizes be employed to avoid spurious conclusions.

Two leading biological systems that are essential for functional genomics and systems biology studies are mixtures of macromolecules in solution (e.g. cell lysates and intact cells.) The value of these systems can be enhanced when the capability of studying the impact of changes to physical and biochemical environments can be studied in real time.

The leading tools currently used in functional genomics and systems biology are mass spectrometry and multiplexed fluorescent microscopy. Both are powerful tools that have proven to be valuable, but both require some form of sample preparation that make them incompatible with real time analysis of the impact of changes to the environment of intact cells at the single molecule level with statistically significant sample sizes.

Both confocal microscopy and TIR microscopy suffer from the need to label the macromolecules. These labels can interfere with the biological function of the molecules to which they are labeled. Also, the wash step required to remove unbound labels proves problematic when studying the real time effects of changes to the cellular environment. The problems associated with the wash step can be eliminated with the use of GFP fusion proteins; however, these fusions can also alter the biology being studied.

In accordance with the present invention, surface plasmon enhanced illumination (SPEI) can be advantageously employed to implement an array based technique that can be used to study macromolecules and their interactions in solution, and to investigate cell surface phenomena in intact cells. Apparatus using SPEI may be employed to study many different unlabeled macromolecules in parallel. This technique identifies the molecule using signatures that are isolated within a rich data set that is based on the macromolecules' interactions that yield measurable photonics effects or signatures as described below. These signatures are the result of the effects of the interactions occurring at a single aperture, and therefore many signatures can be captured simultaneously. This new technique may further incorporate a microfluidics system to deliver environmental changes to the biochemistry substrate or the intact cells, thereby allowing the user to control or alter the biochemical and/or physical environment to test their hypotheses.

Figure 25:
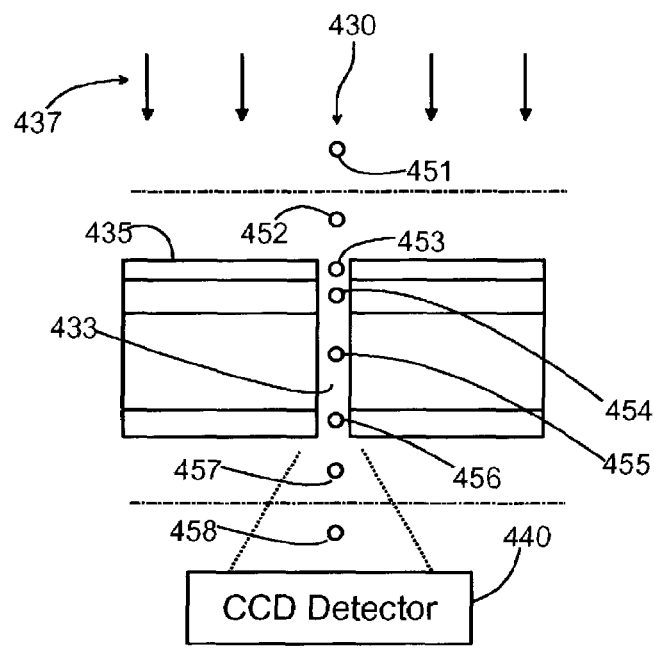
FIG. 25 is a schematic diagram of a flow-through sensor system for analyzing macromolecules.

A first arrangement for measuring changes in emitted light when there are protein or nucleic acid molecules in or near the apertures of a SPEI array is illustrated in FIG. 25. The molecules 430 approach an aperture 433 in the SPEI array 435. The SPEI array 435 is illuminated with broadband or white light as indicated at 437. A CCD detector 440 detects changes in the intensity of light transmission through the aperture 433. Alternatively, changes in the local resonant frequency which will change what wavelength of light is optimally transmitted through that aperture may be detected. Electrophoresis or diffusion may be employed to direct the protein molecules into the aperture 433. Alternatively, the device can be illuminated with monochromatic light that is scanned across the UV-visible-IR portion of the electromagnetic spectrum and the intensity monitored as the wavelength is scanned. Changes in the emission spectra from the apertures indicate the presence and identity of the molecules affecting the changes.

In an alternative arrangement, only a narrow band of light wavelengths would be monitored to detect specific conditions, such as the concentration of a particular protein in solution. The front side of the SPEI array may be illuminated with light at a resonant (optimally-transmitted) wavelength for the device, and intensity data are acquired from the back side of the array for each aperture individually. When protein molecules are added to the buffer solution, shifts in resonances, or changes in light emission from an aperture, may be detected as changes in intensity of the light coming through each aperture individually. For other applications, the SPEI array may be illuminated with light at multiple wavelengths, and the light from each aperture may be detected at multiple wavelengths.

As a protein molecule 430 approaches the SPEI array 435, then moves through an aperture 433 and out the other side, there are five regions where data will be collected and analyzed for possible contributions to signatures that can be used to distinguish between different macromolecules. These are shown schematically in FIG. 25 at 451, where the molecule is approaching an aperture but not yet in the near field of the array 435; at 452 where the molecule is approaching an aperture within the near field of the top of the SPEI array 435; where the molecule is within the aperture at 453 (adjacent the "good metal" surface); at 454 adjacent the interior "bad metal" layer; at 455 adjacent the dielectric layer; at 456 adjacent the "bad metal" exit surface of the SPEI array; at 457 where the molecule has left the aperture on the emission side and is still within the near-field of the array 435; and finally at 458 where the molecule has moved beyond the near-field of the exit surface of the array.

At each position of the molecule, different effects to be measured, including:

a. Changes from the baseline signal measured when only a buffer solution is present at the position without macromolecules.

b. Changes of the SPEI emission intensity or resonance shift due to local change in index of refraction (more likely when the macromolecule is not axially aligned with the aperture);

c. Changes in the emission pattern. Since the material on the bottom side of the array is different from the material on the top side, the emission pattern becomes non-symmetric (more likely when the macromolecule is off-axis). Further, the solution on the emission side can set up a resonance for surface plasmons in the bottom metal layer, which would cause the emission to become fuzzy, possibly recreating the prolate pattern that was eliminated by adding the second metal. The presence of macromolecules at various stages may create measurable scattering of the emitted light.

d. Changes in intensity due to absorption of emitted light.

e. Measurable fluorescence for some molecules.

FIGS. 29 to 32 illustrate the kind of features which may be revealed by the apparatus described in FIGS. 23-26.

Figure 29:
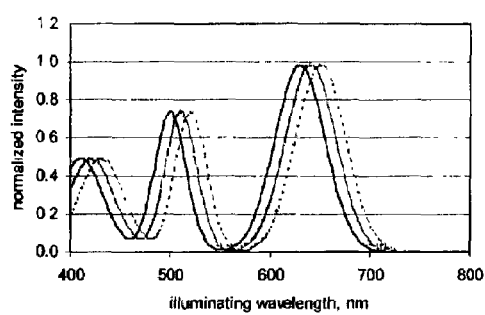
FIGS. 29 through 32 are intensity charts illustrating data that may be acquired by the object analysis mechanisms shown in FIGS. 25-28.

FIG. 29 is an illustration of intensity data which shows the variation of intensity vs. the wavelength of the illumination for a saline buffer at 461, for the buffer with protein at 464, and for the buffer with nucleic acid at 467. Note that FIGS. 29 to 32 are illustrative of the manner in which molecular characteristics may be manifested by intensity data, and do not reflect actual data.

Figure 30:
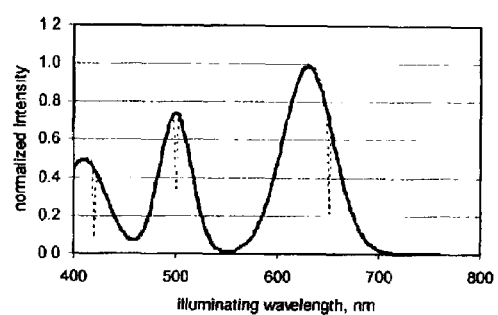

FIG. 30 illustrates the variation of intensity vs. illumination wavelength which manifests absorbance changes, with the solid line 472 indicating a baseline saline buffer and the dotted line indicating the buffer with an added macromolecule.

Figure 31:
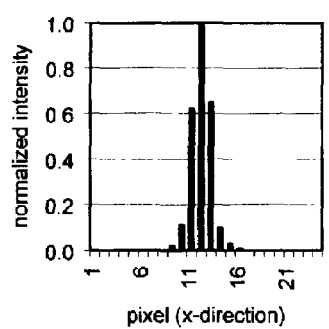
Figure 32:
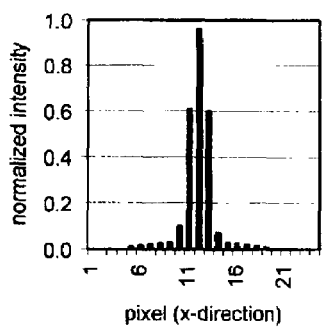

FIGS. 31 and 32 are histograms showing the normalized intensity distribution of the emitted light from a baseline solution exhibiting little or no scatter and intensity distribution data measured when a molecule(s) are added to the solution causing the emission pattern to scatter.

These measurements will be used to extract specific types of information about the macromolecules. Measured light scattering and pattern changes may be used to determine the size, shape and/or orientation of the macromolecules in the solution. Alterations in the SPEI coupling effect may be measured to indicate the size, shape and orientation of the molecules as well as their dielectric constant. Changes in the intensity of the emitted light may be measured to indicate the size, shape and orientation of the molecules as well as their absorbance and transmission characteristics. The spectral content of the emissions may be used to indicate the degree to which the fluorescence of the molecules.

The advantages of SPEI may be utilized in a static (non-flow) system for analyzing proteins and nucleic acids.

Figure 26:
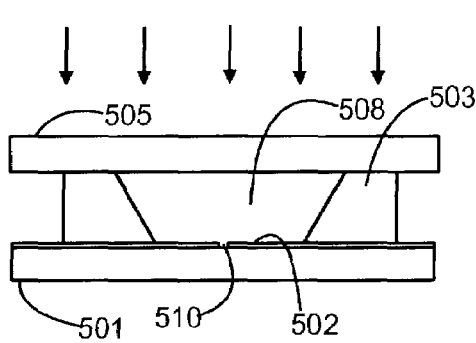
FIGS. 26-28 are side elevational views of different support structures that may be used to construct a sensor for analyzing macromolecules.

As shown in FIG. 26, the arrangement of the stacked combination glass bottom cover 501, an SPEI array 502 formed from a 150 nm thick silicon nitride membrane, a silicon support member 503, and a glass top cover 505. The SPEI array directly abuts the bottom glass cover plate 501. The silicon support 503 spaces the top and SPEI array apart by a distance of approximately 200 µm (micrometers) and forms a shaped reservoir 508 200 µm deep and 600×600 µm square above the an aperture 510 in the silicon nitride membrane 502. This structure thus forms an enclosed gap on the illumination side having a volume of approximately 68 nL that is used as a fluid reservoir to hold the solution containing the biological macromolecules.

To use the apparatus shown in FIG. 26, the upper surface of the SPEI array membrane 502 to which the support member 508 is affixed is wetted with the solution, the array membrane 502 and the support member 503 is set onto cover glass bottom 501, and is then covered with the second cover glass 505 to prevent evaporation of the sample during the time it is being observed and measured.

A SPEI array may also be used in a system employing means to transport the cells or molecules to be examined to the array. For example, for cell experiments, the illuminated side of the SPEI array needs to come in contact with, or in very close proximity to, the cells being investigated.

Figure 27:
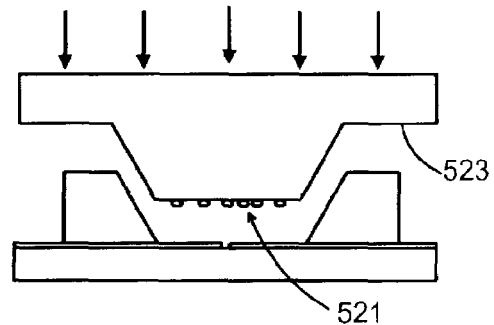

As shown in FIG. 27, the cells 521 may be grown on the surface of a transparent member 523 which is shaped to mate with and be received within the cavity 527 formed in a silicon support member 529 that is affixed to the upper surface of a SPEI array 530. The silicon support member preferably has the same dimensions as noted above for the support member 503 shown in FIG. 26.

Figure 28:
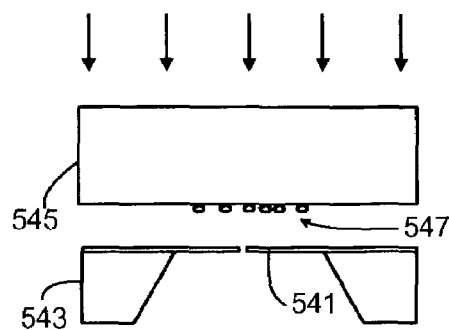

An alternative transport structure is shown in FIG. 28 in which an SPEI array 541 and an attached support member 543 are inverted such that the emission side of the SPEI array is attached to the support frame 541 and the free side of the SPEI array 541 is illuminated through a transparent member 545 on which the cells 547 are grown. This structure increases the working distance (the path length from the array 541 to the collection lens (not shown) and thereby decreases the maximum numerical aperture (NA) of the lens system being employed for collection. This will also decrease the resolution (which is inversely related to the numerical aperture, NA), and also decreases the signal collected or measured (which is inversely proportional to the square of the numerical aperture). The decrease in resolution is may be made less problematic if the array aperture is surrounded by dimples as shown in FIG. 23 or by an annular groove as shown in FIG. 24. However, when closely-spaced apertures are used, the increased working distance could cause light from adjacent apertures to overlap in the CCD camera image, and the decrease in transmission may be a problem when the system is being operated near the limit of its sensitivity. If either resolution or transmission is a problem, the structure shown in FIG. 25 may be employed. A third alternative, reducing the thickness of the support frame, or to eliminate the support frame altogether, is also possible, but such a construction may be too fragile for some applications.

Applying a voltage across the array will cause charged macromolecules to migrate through the array (electrophoresis). The rate of migration of a macromolecule in a particular fluid depends on its charge (in that solution and at that pH) and its characteristic fluidynamic radius, which determines its drag in that fluid. The conductive metal layers of the array will also affect the electric field inside the apertures. Accordingly, the magnitude of voltage applied to create the electric field should be chosen to move the macromolecules through the array at speeds compatible with the data acquisition rate.

In some applications, the externally-applied electric field may affect the behavior of the transmission and resonance characteristics of the SPEI arrays. If the electrical field adversely affects performance, it may be used to transport the molecules to the desired position, and then be shut off the field while making measurements. The electric field may be generated or applied to cause flow, then the field shut off while observing emitted light from each aperture as a function of time. Fast electrical switching circuitry may be employed bring the field rapidly to zero, and an oscillating electrical field produced by a waveform generator may be used to produce electric fields having different frequencies and pulse shapes. By properly applying the motion inducing field, molecules within the apertures or at other desired states within the flow path as enumerated above in connection with FIG. 25.

In a perfusion system, reagents may be delivered in real-time to the cells being studied by micromachining or otherwise effecting fluid paths into the cover glass below the array (on the emission side). The molecules will exit from the perfusion system into a small gap between the bottom cover glass and the array, then move by diffusion through the array to the cells being studied. Electrophoresis may be used to draw molecules released from the cells through the array apertures. By having electrodes in various locations, and alternately connecting and disconnecting various pairs, electrophoresis may be employed to drive molecules through the perfusion system as well. Alternatively, a slight fluid pressure may be applied to the external ports of the microfluidic passages to cause flow.

The technique described above in connection with FIGS. 25-32 enables single cell proteomics, or the study of macromolecules at the single molecule detection level for the contents of a single cell. These techniques are particularly useful when the functional genomics data generated by the measurement instrument are coupled to physiological data gathered from the cell prior to extracting the cellular contents for analysis. In addition, this SPEI analysis technique may be applied to the study of cell surface phenomena such as the extracellular composition of human progenitor cells differentiating. This instrument may be used to analyze the composition of the extracellular fluid in near real-time as factors (e.g. EGF, HGF, LIF) are added or removed from contact with the cells. This allows the study of cells at the single cell level to determine the course of differentiation and to improve understanding of how it might be controlled. The instrument may be used by developmental biologists and tissue engineers, and may be employed to the study of extracellular fluid including the study of the production of insulin by pancreatic islet cells in response to biochemical stimuli.

The sensor described above can also be used to determine the sizes and concentrations of proteins in a complex mixture as is currently done in a one dimensional SDS polyacrylimide gel electrophoresis (1D-SDS PAGE) conducted under denaturing conditions. With this approach the size and concentration information is generated one protein molecule at a time by monitoring the amount of time that a denatured protein takes to transit one of the apertures in a surface plasmon enhanced illumination (SPEI) device by monitoring the length of time during which the resonance of the SPEI device is shifted. By assembling many SPEI apertures in parallel (either single emitting aperture resonant patterns or a full array of emitting apertures) the size and concentration data are acquired. This is routinely done in biology laboratories and shifts in biological research trends will render the gel systems cumbersome as increasing numbers of samples are analyzed. This invention provides a means of performing these analyses in an automated and high throughput manner that is compatible with the increasing numbers of samples to be analyzed.

Figure 2:
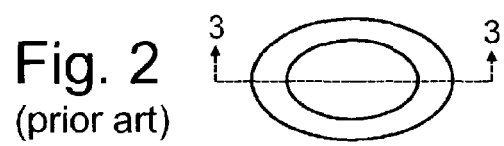
FIG. 2 is a view illustrating the approximate size of the oblong-shaped area illuminated by the light transmitted through the aperture in the film shown in FIG. 1.
Figure 3:
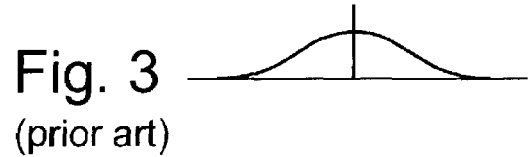
FIG. 3 is a graph illustrating the illumination intensity in the illuminated area taken along the line 3-3 of FIG. 2.

It should be further noted that the structures and techniques described above in connection with FIGS. 25-32 may also employ apertures formed in a monometallic film as described in connection with FIGS. 1-3, rather than a structures in which means are employed for limiting the extent of electronic excitation induced in the surface adjacent to the aperture exit. Although the resolution of such monometallic array structures is more limited, they may be used to implement the biological sensing devices described where high packing densities are not required.

Figure 33:
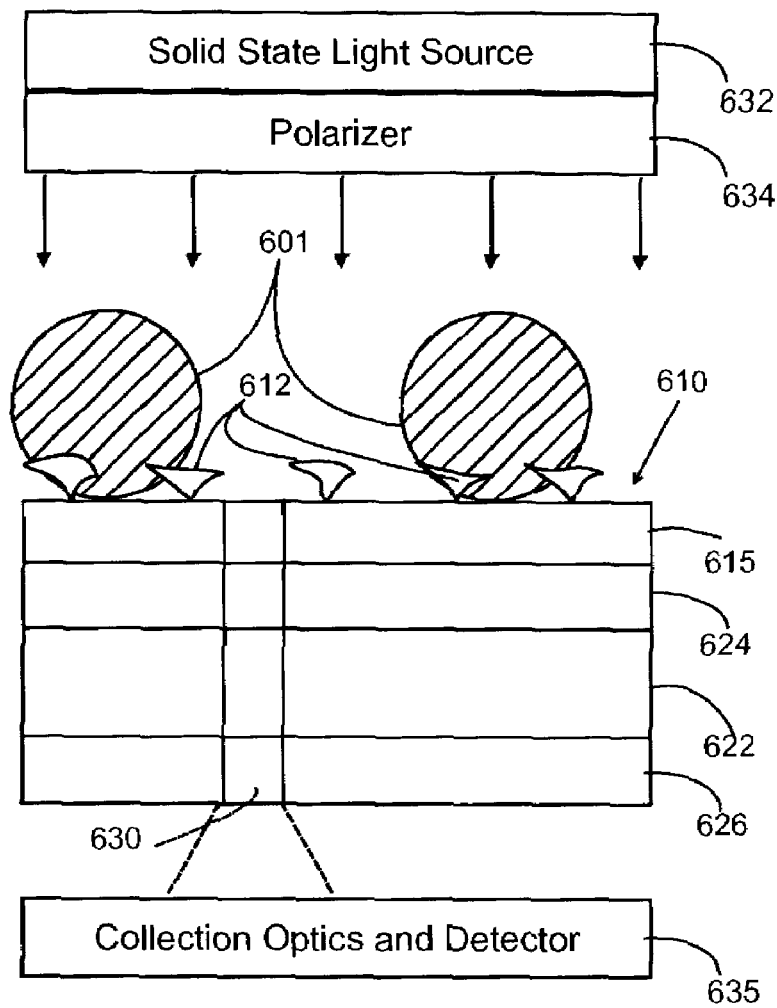
FIG. 33 is a schematic diagram of a sensor for analyzing ligands which are immobilized at the conductive surface of a hole array and their binding partners.

In accordance with the invention, SPEI can be used to implement a biosensor in which ligands are immobilized at the illuminated surface of the SPEI array, and a shift in resonance or other measurable change is measured as the ligands' binding partners bind to the illuminated surface. As illustrated in FIG. 33, ligands 601 are immobilized at the illuminated surface of an SPEI device indicated generally at 610. The ligands' binding partners, the spores shown at 612, bind to the illuminated surface of the upper "good metal" layer 615 of the device 610. Alternatively, the binding partners can be nucleic acids, proteins and protein complexes, cells, and organisms. As described earlier, the SPEI device further comprises a dielectric 622 sandwiched between "bad metal" layers 624 and 626, with the bad metal layer 624 being adjacent to the illuminated good metal layer 615 and the bad metal layer 626 forming the exit surface for illumination passing through the aperture 630. The illustrative embodiment of an SPEI biosensor shown in FIG. 33 further includes a solid state light source 632, a polarizers 634 for the incident light which illuminates the surface of the good metal 615, a support (not shown) for the SPEI device 610, and a collection lens and an arrayed detector shown at 635. Note that other sources of illumination may be used and the light need not be polarized.

The binding effectively alters the electron mobility in the "good" metal layer 615 and changes the resonance condition allowing the light to no longer be constrained to the condition of exiting from the aperture 630. For small amounts of smaller molecules, such as proteins, the shift in pattern size is somewhat minimal, but a resonance shifts (i.e., changes in the wavelength of peak transmission) may be detected. In addition the binding of small molecules to proteins, post translational modifications of proteins, protein-protein interactions, and the binding of nucleic acids can all be detected.

The biosensor illustrated in FIG. 33 preferably employs apertures which are surrounded by spaced dimples as illustrated in FIG. 23, or by an annular groove as shown in FIG. 24. This technique allows the extraordinary transmission to be retained while only providing emission from the central aperture (seen at 630 in FIG. 33). This central aperture then becomes the light source that is monitored to detect and quantify the binding events. Alternatively, a square or hex pattern (or any regular geometric pattern) of apertures can be employed. In this arrangement, independent zones can be established with separation between them and either a spectral shift, resonant shift at any of the apertures is indicative of a positive result. The magnitude of the shift is indicative of the number of binding events and the size of the bound molecules.

The SPEI array for the biosensor may be constructed using a linear array of at least two apertures. For maximum packing density of sets or arrays, polarized light should be used. The polarization direction should be parallel to the length of the array or set. Using unpolarized light does not affect the resonance of the sets or arrays but allows communication of surface plasmons in adjacent sets or arrays effectively making the set or array in question substantially larger. As an example of a single aperture resonant set employing polarized light, FIG. 34 is provided. FIG. 34 shows such a set, this minimal set comprises an aperture 651 flanked on each side by dimples 653 and 655, with the square aperture 651 and the dimples 653 and 655 being aligned in the direction of polarization indicated by the arrow 657. The use of square apertures serves to eliminate variations in the lattice constant by ensuring that the aperture-to-aperture spacing is uniform in the direction of polarization. As in FIGS. 23 and 24, the outside apertures are dimples that are deeper than the skin depth, thereby contributing to the resonant effect but not emitting light. The packing density afforded by this geometry is substantially higher than in arrays in which there is no hole/hole communication (i.e. an array of through holes). The configuration of FIG. 33 also increases the sensitivity of the device. As described above, all of the apertures in this pattern can also penetrate the device and emit light, and a shift at any of the apertures indicates a positive result.

The figures and discussion have described ligands bound to the illuminated side only. It is possible that the ligands could be bound to the non-illuminated side of the array. In this case, the array spacing of periodic surface features on the illuminated side could be tailored such that dramatic changes in resonance could be seen when the top (illuminated surface) resonated with the bottom (non illuminated) surface. This could be done with several sets of arrays of differing lattice constants so that different concentrations or different targets could be detected.

Ligands for specific targets of interest (chemical or biological agents, viruses, nucleic acids, proteins and protein complexes, carbohydrates etc.) may be immobilized on the surface of the SPEI device. As the targets bind with these ligands in the near-field of the metal, the electron mobility in the metal surface will be altered, thereby changing the resonant frequencies of that surface and thereby altering the character (spectral transmission and pattern of emission) of the light emitted from exit surface of the array. The same device and principles can be used to detect secondary reactions to molecules that have been bound to the ligands. An important example of secondary reactions is the post-translational modification of proteins. One can also make use of a secondary reaction to amplify a signal. An example of this amplification is the use of a secondary antibody or other ligand to the molecules that have bound to the immobilized ligands. This secondary antibody is conjugated to something (e.g. gold particles) that will increase the change in the electron mobility of the illuminated surface, thereby "amplifying" the signal.

The same effect is monitored in the commonly used ATR (attenuated total reflection) surface plasmon resonance instruments (called "SPR" instruments) by measuring the angle at which resonance is established with a fixed wavelength of narrow bandwidth or by varying the wavelength at a fixed angle. In these instruments, when resonance exists, the normally "totally" reflected photons are mostly absorbed marking resonance.

The SPEI biosensor of FIG. 33 may be fabricated in different ways to analyze different sample sizes.

Alternative architectures for the biosensor include the use of a free standing monometallic film and a monometallic film on a transparent substrate. All of the binding and detection methods remain the same.

A small area detector on which ligands will be bound is used to detect single molecules, or a very small number of molecules. By increasing the number of binding sites, the rate at which the molecule can be detected in small concentrations increases linearly with the number of sites. In this configuration, there are tradeoffs to be made for speed. The previously described multi-layer dielectric/metallic stack shown in FIG. 33 allows a very high packing density. It does, however, suffer from lower transmission than does a monometallic film. While the monometallic film may show better transmission, it may not allow maximum packing density of patterns. For very large molecules, transmission is not an issue as changes are sensed abruptly with even very low transmissions. For smaller molecules, though, the sensitivity of the collection optics is the limiting factor and higher transmissions mitigate some of this dependence. In operation, this arrangement will display behavior similar to a Geiger counter showing a count and a rate.

The second kind of sensor employs a large number of repeating patterns to which ligands for several targets will be immobilized. The ligands for any specific compound will be immobilized in several locations across the surface of the device to provide for redundant detection of the targets.

With repeating patterns, each pattern may comprise two identical subpatterns, one of which serves as the active detection area and the other serves as an internal control, providing a baseline of the emission pattern against which the binding results can be compared. The illumination source may scan through a range of illumination wavelengths as data is collected.

Since a high density can be achieved with this type of biosensor, many more repeating patterns may be fabricated than there are targets to be detected. This allows for some of the density to be deployed to achieve redundancy to enhance the fidelity of the data and to use many different ligands for each compound. The use of different ligands for a compound enriches the data set in several ways. First, it provides for even further redundancy. Also because different ligands typically have different binding characteristics (sensitivity, linearity, selectivity), a set can be constructed that spans a broader range of sample concentration and mixture characteristics. An understanding of the binding characteristics of the ligands in a set allows for the result data to be enhanced by computer processing to improve the fidelity and utility of the information generated in the detection process. This also makes the detection more robust in response to mutations, both natural and engineered, in the targets because it is unlikely that all molecular recognition sites will be altered.

Both positive and negative controls may be incorporated into the biosensor design. Negative controls may be provided by immobilizing ligands for the targets of interest where the binding capacity of the ligands has been eliminated. This provides a raw signal against which the positive results can be compared. Positive controls may be provided by immobilizing ligands for a molecule that is not expected to be present in the application and drying some of this molecule onto the device. This molecule would be solubilized when the sample is added and expected to bind to its ligand, thereby providing a positive signal to ensure proper operation of the device.

To use the biosensor seen in FIG. 33, a sample will be applied to the illuminated surface of the SPEI device and incubated to allow binding to occur. During this incubation time the emitted light will be monitored and compared against the internal controls to determine the presence of the targets of interest. This detection scheme will provide kinetics of binding and concentration for the targets.

A microfluidics system and an aperture configuration that eliminates the need for a scanned light source may be employed. The microfluidics system may perform automated sample preparation and permit the instrument to perform studies where the effect of changes to the biochemical composition of the sample solution is monitored. Elimination of the need for a scanned light source can be accomplished by having each ligand bound to a set of patterns with differing lattice constants, therefore of different resonant frequencies and with differing loci of Wood's Anomaly. In this arrangement, as the compound binds to its ligands the resonant frequencies of the apertures will shift according to the change in mobility of the electrons in the metal surface and according to the lattice constants of the different sets. The changes seen in the different sets are measured and compared. Through the comparison of the changes in the sets' responses to applied compounds the amount of bound compounds can be determined.

In an illustrative biosensor whose sensitivity has been optimized by calculation using a mathematical model of the good metal surface (see Jung et al., Quantitative interpretation of the response of surface plasmon resonance sensors to adsorbed films. *Langmuir* 14, 5636-5648 (1998)), a peak resonance of 2 nm was assigned for a positive detection of the molecules of interest. For maximum sensitivity the following assumptions were been made in the calculations for large and small bio-molecules:

1) The molecules of interest are proteins and have an index of refraction of $1.6^{22}$ and $k=0^{21}$
2) In a solution, in which there are proteins, the proteins are all bound to the ligands (i.e. there exist no unbound proteins and the index of the solution is equivalent to the index of the solvent by itself
3) Water is assumed to be the solvent at 20 degrees C. (n=1.3345)
4) The height of the solvent layer above bound proteins is zero; immediately above the protein layer is a medium of index of unity. The height of the solvent layer adjacent to bound proteins is equivalent to the thickness of the protein layer
5) The thickness of ligand layer is defined as 10 nm and the index of refraction of the ligands is n=1.6, k=0
6) The shape of the resonant device is that shown in FIG. 34.
7) The entire area of the resonant pattern (excluding the hole(s) and dimples (or annuli)) is uniformly weighted as far as collection of photons and contribution to surface plasmon resonance
8) The incoming light is polarized and aligned with the dimples
9) The characteristic near-field decay length, $I_d$, is $\lambda/4$
10) The hole size is 100 nm (smaller holes increase sensitivity)
11) The lattice constant is 500 nm
12) The collector metal (good metal) is aluminum with dielectric function according to the *Handbook of Optical Constants of Solids* (ed. Palik, E.) (Academic Press, Orlando, 1985) at a wavelength of illumination of 564 nm (the resonance of a clean (ligands at 10 nm with a water layer of thickness 30 nm and air above)
13) The index of "everything else" is unity
14) Protein molecules are assumed to be cubes with characteristic dimension of edge length 30 nm
15) Changes in surrounding indices of reflection are conservatively assumed not to affect total transmission For large molecules such as the spores of *B. anthracis* whose characteristic dimension is 300 nm, the sensitivity of the device is such that one spore yields a change in peak wavelength of 143 nm. This change can also be validated by a measurable change in the prolate pattern shape.

For small molecules such as individual proteins whose characteristic dimension is assumed to be 30 nm, the sensitivity of the device is 4 protein molecules yielding a change in peak wavelength of 1.91 nm. Of course, smaller molecules can be detected in higher bound concentrations.

The sensitivity is governed, among other things, by the lattice constant and the size of the hole. Smaller lattice constants and smaller holes both make for higher sensitivities as both contribute to the area to which the ligands, and, hence proteins, can be bound. The smaller the ratio of the binding area, $2(\rho-s)s$ (for the pattern in FIG. 9) (where $\rho$ is the lattice constant and s is the hole characteristic dimension), to the characteristic dimension of the protein ($\Phi$) and number of protein molecules (v), $\phi/v\phi^2$, the more sensitive the device will be. Several tradeoffs must be made when designing these devices. Very thin devices will be fragile, while thicker devices, although less fragile, will not allow small holes to be milled. Shorter wavelengths also increase the sensitivity (by allowing smaller lattice constants) but intense UV may alter the properties of the bio-molecules and affect their binding.

Larger holes than the minimum that can be fabricated may be selected. The smallest distribution of hole sizes is achieved when hole aspect ratio is smaller than 4. Narrow distributions of hole size and lattice constants allow sharper resonances.

The area of the device (and packing and number of resonant patterns) is largely dependent on the minimum volume of solvent that can be dispensed onto the resonant patterns. For minimum sensing times, a minimum of volume should be distributed over a maximum area with as close packing of resonant patterns as possible. Also, the collection array or device that collects the photons emitted from the resonant patterns should have a very high signal to noise ratio and should be as sensitive as possible. Because the transmission of the SPEI devices appears to be independent of irradiance levels, arrayed detectors such as CCDs without single photon sensitivities can be used by simply increasing the irradiance levels to achieve a satisfactory signal to noise ratio.

CONCLUSION

It is to be understood that the specific embodiments and applications of the invention that have been described are merely illustrative applications of the principles of the invention. Numerous modifications may be made to the methods and apparatus described without departing from the true spirit and scope of the invention.

What is claimed is:

1. Apparatus for analyzing at least one small object comprising,
   a source of electromagnetic radiation,
   a radiation detector,
   a substantially planar light barrier interposed between said source and said radiation detector, said light barrier including a first electrically conductive surface on which the electromagnetic radiation from said source is incident, and
   at least one aperture through said light barrier, said aperture having a width in at least one dimension that is smaller than one wavelength of said electromagnetic radiation, at least some of said electromagnetic radiation passing from said source through said aperture to said radiation detector,
   wherein:
   a presence of said at least one small object in close proximity to said first electrically conductive surface causes a change in a resonance condition of said light barrier;
   said change in the resonance condition of said light barrier causes variations in said electromagnetic radiation; and
   said radiation detector is positioned with respect to the light barrier to receive said electromagnetic radiation exiting from the light barrier without significant alterations to said variations, so as to detect said variations in said electromagnetic radiation resulting from the change in the resonance condition of said light barrier due to the presence of said at least one small object in close proximity to said first electrically conductive surface.

2. Apparatus for analyzing at least one small object as set forth in claim 1 wherein said light barrier further includes a second surface on an opposite side of said barrier from said first electrically conductive surface, said second surface being adjacent to said radiation detector, wherein said aperture passes from said first surface to said second surface, and wherein said barrier further includes means for limiting the extent of electronic excitation induced in said second surface in the vicinity of said aperture by the incident light from said source.

3. Apparatus for analyzing at least one small object as set forth in claim 2 wherein said means for limiting the extent of the electronic excitation induced in said second surface in the vicinity of said apertures comprises a barrier material that is opaque to the transmission of said electromagnetic radiation formed in said light barrier and positioned between said first electrically conductive surface and said second surface.

4. Apparatus for analyzing at least one small object as set forth in claim 2 wherein said first electrically conductive surface is formed by a layer of conductive metal having a thickness greater than the skin depth of said metal at the frequency of said electromagnetic radiation.

5. Apparatus for analyzing at least one small object as set forth in claim 1 wherein said small object is positioned adjacent to said first electrically conductive surface in a vicinity of said at least one aperture.

6. Apparatus for analyzing at least one small object as set forth in claim 1 wherein said small object is contained in a fluid and wherein the apparatus further comprises a reservoir for holding said fluid, said reservoir being positioned adjacent to said first electrically conductive surface.

7. Apparatus for analyzing at least one small object as set forth in claim 1 further comprising at least one binding object to which said small object is attached, said binding object being immobilized adjacent to said first electrically conductive surface.

8. Apparatus for analyzing at least one small object as set forth in claim 7 wherein said binding object binds to said first electrically conductive surface.

9. Apparatus for analyzing at least one small object as set forth in claim 8 wherein said binding object includes at least one ligand.

10. Apparatus for analyzing at least one small object as set forth in claim 8 wherein an attachment of said small object to said binding object changes the resonance condition of said light barrier.

11. Apparatus for analyzing at least one small object set forth in claim 1 wherein said aperture has a width in at least one direction that is between 2 nm and the dimension defined by the Rayleigh criterion for said frequency of electromagnetic radiation.

12. Apparatus for analyzing at least one small object as set forth in claim 1 wherein said barrier comprises a metallic film affixed to a substrate that is transparent to said electromagnetic radiation.

13. Apparatus as set forth in claim 12 wherein said aperture extends through said metallic film but not through said substrate.

14. Apparatus for analyzing at least one small object as set forth in claim 1 further comprising a transparent support member to which said small object is attached.

15. Apparatus as set forth in claim 1 wherein said small object is a macromolecule.

16. Apparatus set forth in claim 1 wherein said small object is a biological macromolecule.

17. Apparatus set forth in claim 1 wherein said small object is a protein complex.

18. Apparatus set forth in claim 1 wherein said small object is post-translational modification of a protein or a protein complex.

19. Apparatus set forth in claim 1 wherein said small object is a binding of a protein to a nucleic acid.

20. Apparatus set forth in claim 1 wherein said small object is a biological organism.

21. Apparatus set forth in claim 1 wherein said small object is a spore.

22. Apparatus as set forth in claim 1 wherein said small object is a protein molecule.

23. Apparatus as set forth in claim 1 wherein said small object is a nucleic acid molecule.

24. Apparatus as set forth in claim 1 wherein said small object is a single cell.

25. Apparatus as set forth in claim 1 wherein said variations in said electromagnetic radiation include intensity variations.

26. Apparatus as set forth in claim 1 wherein said variations in said electromagnetic radiation include variations in a spectrum of said electromagnetic radiation.

27. Apparatus as set forth in claim 1 wherein said variations in said electromagnetic radiation include changes in an emission pattern of the radiation impinging on said radiation detector.

28. Apparatus for analyzing small objects comprising, in combination,
 a source of electromagnetic radiation,
 a radiation detector,
 a substantially planar light barrier interposed between said source and said radiation detector, said light barrier defining a first electrically conductive surface on the side of said barrier exposed to incident light from said source,
 at least one aperture through said light barrier, said aperture having a width in at least one dimension that is smaller than one wavelength of said electromagnetic radiation and larger than said small objects,
 means for causing said small objects to migrate through said aperture, and
 means coupled to said radiation detector for measuring variations in the electromagnetic energy passing through said aperture as said small objects migrate through said aperture.

29. Apparatus for analyzing small objects as set forth in claim 28 wherein said light barrier further defines a second surface on the opposite side of said barrier, said second surface being adjacent to said radiation detector, wherein said aperture passes from said first surface to said second surface, and wherein said barrier further comprises means for limiting the extent of electronic excitation induced in said second surface in the vicinity of said aperture by the incident light from said source.

30. Apparatus for analyzing small objects as set forth in claim 29 wherein said means for limiting the extent of the electronic excitation induced in said second surface in the vicinity of said apertures comprises a barrier material that is opaque to the transmission of said electromagnetic radiation formed in said light barrier and positioned between said first electrically conductive surface and said second surface.

31. Apparatus for analyzing small objects as set forth in claim 29 wherein said first electrically conductive surface is formed by a layer of conductive metal having a thickness greater than the skin depth of said metal at the frequency of said electromagnetic radiation.

32. Apparatus for analyzing small objects as set forth in claim 31 wherein said layer of conductive metal extends into the interior side walls of each of said aperture terminating at said second surface in a limited area in the vicinity of said aperture.

33. Apparatus as set forth in claim 28 wherein said aperture has a width in at least one direction that is between 2 nm and the dimension defined by the Rayleigh criterion for said frequency of electromagnetic radiation.

34. Apparatus for analyzing small objects as set forth in claim 28 wherein barrier comprises a dielectric that exhibits a bandgap that is larger than the frequency of said electromagnetic radiation.

35. Apparatus for analyzing small objects as set forth in claim 28 wherein said electrically conductive surface is constructed of a layer of a first metal and wherein said barrier material is a different metal characterized in that said conductive surface and said barrier material have substantially different resonances.

36. Apparatus for analyzing small objects as set forth in claim 28 wherein said electrically conductive surface is formed by metallic layer affixed to a substrate that is transparent to said electromagnetic radiation.

37. Apparatus for analyzing small objects as set forth in claim 28 wherein said small objects are macromolecules.

38. Apparatus for analyzing small objects as set forth in claim 28 wherein said small objects are biological macromolecules.

39. Apparatus for analyzing small objects as set forth in claim 28 wherein said small objects are protein molecules.

40. Apparatus for analyzing small objects as set forth in claim 28 wherein said small objects are nucleic acid molecules.

41. Apparatus for analyzing small objects as set forth in claim 28 wherein said small objects are single cells.

42. Apparatus set forth in claim 28 wherein said small object is a protein complex.

43. Apparatus set forth in claim 28 wherein said small object is post-translational modification of a protein or a protein complex.

44. Apparatus set forth in claim 28 wherein said small object includes a protein bound to a nucleic acid.

45. Apparatus set forth in claim 28 wherein said small object is a biological organism.

46. Apparatus set forth in claim 28 wherein said small object is a spore.

47. Apparatus for analyzing small objects as set forth in claim 28 wherein said means coupled to said radiation detector for measuring variations in the electromagnetic energy passing through said aperture as said small objects migrate through said aperture comprises means for measuring changes in the intensity of the radiation passing through said aperture.

48. Apparatus for analyzing small objects as set forth in claim 28 wherein said means coupled to said radiation detector for measuring variations in the electromagnetic energy passing through said aperture as said small objects migrate through said aperture comprises means for measuring changes in resonance which alters the amount of the electromagnetic energy passing through said aperture as said small objects migrate through said aperture of the radiation passing through said aperture.

49. Apparatus for analyzing small objects as set forth in claim 37 wherein said means for measuring changers in resonance includes means for measuring variations in the intensity of said electromagnetic radiation vs. the wavelength of said radiation.

50. Apparatus for analyzing small objects as set forth in claim 28 wherein said means coupled to said radiation detector for measuring variations in the electromagnetic energy passing through said aperture as said small objects migrate through said aperture comprises means for measuring changes in the emission pattern of the radiation passing through said aperture to said radiation detector.

51. Apparatus for analyzing small objects as set forth in claim 28 wherein said means coupled to said radiation detector for measuring variations in the electromagnetic energy passing through said aperture as said small objects migrate through said aperture comprises means for measuring changes in the intensity of the radiation passing through said aperture due to the absorption of radiation by said small objects.

52. Apparatus for analyzing small objects as set forth in claim 28 wherein said means coupled to said radiation detector for measuring variations in the electromagnetic energy passing through said aperture as said small objects migrate through said aperture comprises means for measuring the fluorescence of said small objects which are exposed to said electromagnetic radiation.

53. Apparatus for analyzing small objects as set forth in claim 52 wherein said means for measuring the fluorescence of said small objects comprises means for measuring the spectral content of the radiation detected by said radiation detector.

54. Apparatus for analyzing small objects as set forth in claim 28 wherein said means coupled to said radiation detector for measuring variations in the electromagnetic energy passing through said aperture as said small objects migrate through said aperture comprises means for measuring said variations as each of said small objects occupies a different position with respect to said aperture.

55. Apparatus for analyzing small objects as set forth in claim 28 wherein said small objects are electrically charged and wherein means for causing said small objects to migrate through said aperture comprises a source of an electrostatic field.

56. Apparatus for analyzing small objects as set forth in claim 28 wherein said small objects are contained in a liquid carrier and wherein said means for causing said small objects to migrate through said aperture comprises a source of fluid pressure applied to said liquid carrier.

57. Apparatus for analyzing small objects as set forth in claim 56 wherein said source of fluid pressure comprises a fluidics supply system providing a fluid passageway coupled to said aperture for conveying said liquid carrier and said small objects through said aperture.

58. Apparatus for analyzing small objects as set forth in claim 57 wherein said means coupled to said radiation detector for measuring variations in the electromagnetic energy passing through said aperture as said small objects migrate through said aperture comprises means for measuring said electromagnetic energy when said liquid carrier alone is in said aperture and measuring said electromagnetic energy when said liquid carrier and at least one of said small objects is in or adjacent to said aperture.

59. A measurement instrument for concurrently analyzing a plurality of biological macromolecules, said device comprising, combination,
   a source of electromagnetic radiation,
   a substantially planar light barrier positioned between said source and said target, said light barrier being opaque to said electromagnetic radiation, defining a first surface facing said source and a second surface facing said target, and further comprising of a layer of metal affixed to said first surface,
   an array of apertures through said light barrier, each of said apertures having a width in at least one direction which is shorter than the wavelength of said electromagnetic radiation and wider than the size of said macromolecules,
   means for causing said biological macromolecules to migrate through said apertures, and
   sensing means for detecting variations in the electromagnetic energy passing through at least selected ones of said apertures as said biological macromolecules migrate through said selected ones of said apertures.

60. A measurement instrument as set forth in claim 59 wherein said layer of metal has a thickness at least as large as the skin depth of said metal at the frequency of said electromagnetic radiation.

61. The device set forth in claim 59 wherein said metal is selected from a group consisting of gold, silver, aluminum, beryllium, rhenium, osmium, potassium, rubidium, cesium, rhenium oxide, tungsten oxide, and copper.

62. A measurement instrument as set forth in claim 59 wherein said light barrier further defines a second surface on the opposite side of said barrier, said second surface being adjacent to said sensing means, and wherein each of said apertures passes from said first surface to said second surface, and wherein said barrier further comprises means for limiting the extent of electronic excitation induced in said second surface in the vicinity of each of said apertures by the incident light from said source.

63. A measurement instrument as set forth in claim 62 wherein said means for limiting the extent of the electronic excitation induced in said second surface in the vicinity of said apertures comprises a barrier material that is opaque to the transmission of said electromagnetic radiation formed in said light barrier and positioned between said first electrically conductive surface and said second surface.

64. A measurement instrument as set forth in claim 59 wherein each of said apertures has a width in at least one direction that is between 2 nm and the dimension defined by the Rayleigh criterion for said frequency of electromagnetic radiation.

65. A measurement instrument as set forth in claim 59 wherein said layer of metal is affixed to a substrate that is transparent to said electromagnetic radiation.

66. A measurement instrument as set forth in claim 59 wherein said biological macromolecules are protein molecules.

67. A measurement instrument as set forth in claim 59 wherein said biological macromolecules are protein molecules.

68. A measurement instrument as set forth in claim 59 wherein said biological macromolecules are nucleic acid molecules.

69. A measurement instrument as set forth in claim 59 wherein said sensing means for detecting variations in the electromagnetic energy passing through at least selected ones of said apertures comprises means for measuring changes in the intensity of the radiation passing through said selected ones of said apertures.

70. A measurement instrument as set forth in claim 59 wherein said sensing means for detecting variations in the electromagnetic energy passing through at least selected ones of said apertures comprises means for measuring changes in resonance which alters the amount of the electromagnetic energy passing through said apertures as said macromolecules migrate through said apertures.

71. A measurement instrument as set forth in claim 59 wherein said means for measuring changers in resonance includes means for measuring variations in the intensity of said electromagnetic radiation passing through said apertures vs. the wavelength of said radiation.

72. A measurement instrument as set forth in claim 59 wherein said sensing means for detecting variations in the electromagnetic energy passing through at least selected ones of said apertures comprises means for measuring changes in the emission pattern of the radiation passing through said apertures to said sensing means.

73. A measurement instrument as set forth in claim 59 wherein said sensing means for detecting variations in the electromagnetic energy passing through at least selected ones of said apertures comprises means for measuring changes in the intensity of the radiation passing through said selected ones of said apertures due to the absorption of radiation by said macromolecules.

74. A measurement instrument as set forth in claim 59 wherein said sensing means for detecting variations in the electromagnetic energy passing through at least selected ones of said apertures comprises means for measuring the fluorescence of macromolecules that are exposed to said electromagnetic radiation.

75. A measurement instrument as set forth in claim 59 wherein said sensing means for detecting variations in the electromagnetic energy passing through at least selected ones of said apertures comprises means for said variations as said macromolecules occupy a different positions with respect to said apertures.

76. A measurement instrument as set forth in claim 59 wherein said biological macromolecules are electrically charged and wherein means for causing said small objects to migrate through said aperture comprises a source of an electrostatic field.

77. A measurement instrument as set forth in claim 59 wherein said biological macromolecules are contained in a liquid carrier and wherein said means for causing said macromolecules to migrate through said aperture comprises a source of fluid pressure applied to said liquid carrier.

78. A measurement instrument as set forth in claim 77 wherein said source of fluid pressure comprises a fluidics supply system providing a fluid passageway coupled to said aperture for conveying said liquid carrier and said macromolecules through said apertures.

79. The apparatus of claim 1, wherein the change in the resonance condition results from a change in a dielectric constant of a medium adjacent to said first electrically conductive surface due to the presence of said at least one small object in close proximity to said first electrically conductive surface.

80. The apparatus of claim 1, wherein the change in the resonance condition results from a change in an effective dielectric constant of said first electrically conductive surface due to the presence of said at least one small object in close proximity to said first electrically conductive surface.

81. The apparatus of claim 80, wherein said first electrically conductive surface includes at least one binding object to facilitate a binding of said at least one small object to said first electrically conductive surface, and wherein the change in the effective dielectric constant of said first electrically conductive surface results from the binding of said at least one small object to said first electrically conductive surface.

82. The apparatus of claim 1, wherein the at least one small object includes a fluid.

83. The apparatus of claim 82, wherein the fluid includes a buffer solution.

84. The apparatus of claim 82, wherein the change in the resonance condition results from a change in a dielectric constant of the fluid.

85. The apparatus of claim 1, further comprising at least one microfluidic system to facilitate a flow of fluid in close proximity to said first electrically conductive surface.

86. The apparatus of claim 82, wherein the fluid includes the at least one small object.

\* \* \* \* \*